(12) United States Patent
Kozian et al.

(10) Patent No.: US 7,892,744 B2
(45) Date of Patent: Feb. 22, 2011

(54) ANALYSIS AND USE OF PAR1 POLYMORPHISMS FOR EVALUATING THE RISK OF CARDIOVASCULAR DISORDERS

(75) Inventors: Detlef Kozian, Hattersheim (DE); Joerg Czech, Marburg (DE); Karl-Ernst Siegler, Ludwigshafen (DE); Jean-Francois Deleuze, Combs la Ville (FR); Sylvain Ricard, Paris (FR); Sandrine Mace, Jouy-En-Josas (FR)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 12/567,942

(22) Filed: Sep. 28, 2009

(65) Prior Publication Data

US 2010/0221714 A1 Sep. 2, 2010

Related U.S. Application Data

(63) Continuation of application No. 10/831,552, filed on Apr. 23, 2004, now abandoned.

(60) Provisional application No. 60/503,732, filed on Sep. 17, 2003.

(30) Foreign Application Priority Data

Apr. 24, 2003 (DE) ................. 103 18 496

(51) Int. Cl.
*C12Q 1/68* (2006.01)
*C12P 19/34* (2006.01)
*C07H 21/02* (2006.01)
*C07H 21/04* (2006.01)

(52) U.S. Cl. ............... 435/6; 435/91.1; 435/91.2; 536/23.1; 536/24.3

(58) Field of Classification Search ............... None
See application file for complete search history.

(56) References Cited

U.S. PATENT DOCUMENTS 5,744,338 A 4/1998 Hodgson et al.
6,316,196 B1 * 11/2001 Morten ............... 435/6

OTHER PUBLICATIONS

Cambien et al; American Journal of Human Genetics, vol. 65, pp. 183-191; 1999.*
Arnaud, Emmanuel et al., Protective Effect of a Thrombin Receptor (Protease-Activated Receptor 1) Gene Polymorphism Toward Venous Thromboembolism, Arterioscler Thromb Vasc Biol., (2000), vol. 20. pp. 585-592.
Schmidt, Valentina A. et al. Genomic Cloning and Characterization of the Human Thrombin Receptor Gene, The Journal Of Biological Chemistry, (1996), vol. 271, No. 16, pp. 9307-9312.
Dupont, Annabelle et al., An intronic polymorphism in the PAR-1 gene is associated with platelet receptor denisty and the response to SFLLRN, Blood, (2003), vol. 101, pp. 1833-1840.
Park, H-Y et al, Identification of New Single-Nucleotide Polymorphisms In The Thrombin Receptor Gene And Their Effects on Coronary Artery Diseases In Koreans. Clinical and Experimental Pharmacology and Physiology, (2000), vol. 27. pp. 690-693.
Schmidt et al., Genbank Accession No. NM_001992 (Oct. 1999).
Cambien et al., Sequence Diversity in 36 Candidate Genes for Cardiovascular Disorders, Am J. Hum Genet., vol. 65, pp. 183-191, 1999.

* cited by examiner

*Primary Examiner*—Jehanne S Sitton

(57) ABSTRACT

The invention relates to polynucleotide sequences comprising genetic variations of the PAR1 gene at positions 3090 and/or 3329. The occurrence of these variants in humans correlates with increased occurrence of particular cardiovascular disorders. The invention furthermore relates to methods for detecting said genetic variations for the purpose of patient diagnosis.

6 Claims, 12 Drawing Sheets

Fig. 1

|  |  | n | % |
|---|---|---|---|
| Total |  | 1404 |  |
| Gender | Female | 406 | 28.9 |
|  | Male | 998 | 71.1 |
| Age |  | 62.7 (30.0 – 90.7) |  |
| BMI* (Body Mass Index) |  | 27.8 (16.7 – 57.1) |  |
| Hypertension |  | 834 | 59.4 |
| Smoker |  | 923 | 65.7 |
| Angina pectoris |  | 210 | 62.7 |
| Diabetic (ADA) |  | 445 | 31.7 |
| Cardiac infarction |  | 579 | 41.0 |
| CAD (> 20% stenosis) |  | 1087 | 78.8 |
| Stroke |  | 106 | 7.5 |

* Medians and quartiles (Q1 – Q3)

Fig. 2

|  | PAR1 C3329C | PAR1 C3329A | PAR1 A3329A |
|---|---|---|---|
| PAR1 T3090T | 1 | 0 | 724 |
| PAR1 /3090C | 0 | 371 | 160 |
| PAR1 C3090C | 51 | 47 | 8 |

Fig. 3

|  |  | 95% - confidence interval |  |  |
|---|---|---|---|---|
|  | odds ratio | lower | upper | p value |
| Atrial fibrillation | 1.97 | 1.18 | 3.30 | 0.0101 |
| Cardiomyopathy | 1.84 | 1.04 | 3.24 | 0.0353 |

Fig. 4

|  | odds ratio | 95% - confidence interval | | p value |
|---|---|---|---|---|
|  |  | lower | upper |  |
| Atrial fibrillation | 2.35 | 1.18 | 4.68 | 0.0149 |
| Cardiomyopathy | 0.36 | 0.17 | 0.79 | 0.0107 |
| Unstable angina | 0.36 | 0.16 | 0.81 | 0.0142 |

Fig. 5

```
ggcgggggc  gcacagagcc  agaggggctt  gcgagcggcg  gctgagggac  cgcggggagg
gggcgccgag  cggctccagc  gcagagactc  tcactgcacg  ccggaggccc  cttcctcgct
ccgcccgcgc  gaccgcgcgc  cccagtcccg  ccccgccccg  ctaaccgccc  cagacacagc
gctcgccgag  ggtcgcttgg  accctgatct  tacccgtggg  caccctgcgc  tctgcctgcc
gcgaagaccg  gctccccgac  ccgcagaagt  caggagagag  ggtgaagcgg  agcagcccga
ggcggggcag  cctcccggag  cagcgccgcg  cagagccgg   gacaatgggg  ccgcggcggc
tgctgctggt  ggccgcctgc  ttcagtctgt  gcggcccgct  gttgtctgcc  cgcacccggg
cccgcaggcc  agaatcaaaa  gcaacaaatg  ccaccttaga  tccccggtca  tttcttctca
ggaaccccaa  tgataaatat  gaaccatttt  gggaggatga  ggagaaaaat  gaaagtgggt
taactgaata  cagattagtc  tccatcaata  aaagcagtcc  tcttcaaaaa  caacttcctg
cattcatctc  agaagatgcc  tccggatatt  tgaccagctc  ctggctgaca  ctctttgtcc
catctgtgta  caccggagtg  tttgtagtca  gcctcccact  aaacatcatg  gccatcgttg
tgttcatcct  gaaaatgaag  gtcaagaagc  cggcggtggt  gtacatgctg  cacctggcca
cggcagatgt  gctgtttgtg  tctgtgctcc  cctttaagat  cagctattac  ttttccggca
gtgattggca  gttttgggtct  gaattgtgtc  gcttcgtcac  tgcagcattt  tactgtaaca
tgtacgcctc  tatcttgctc  atgacagtca  taagcattga  ccggtttctg  gctgtggtgt
atcccatgca  gtccctctcc  tggcgtactc  tgggaagggc  ttccttcact  tgtctggcca
tctgggcttt  ggccatcgca  ggggtagtgc  ctctcgtcct  caaggagcaa  accatccagg
tgcccgggct  caacatcact  acctgtcatg  atgtgctcaa  tgaaaccctg  ctcgaaggct
actatgccta  ctacttctca  gccttctctg  ctgtcttctt  ttttgtgccg  ctgatcattt
ccacggtctg  ttatgtgtct  atcattcgat  gtcttagctc  ttccgcagtt  gccaaccgca
gcaagaagtc  ccgggctttg  ttcctgtcag  ctgctgtttt  ctgcatcttc  atcatttgct
tcggacccac  aaacgtcctc  ctgattgcgc  attactcatt  cctttctcac  acttccacca
cagaggctgc  ctactttgcc  tacctcctct  gtgtctgtgt  cagcagcata  agctcgtgca
tcgaccccct  aatttactat  tacgcttcct  ctgagtgcca  gaggtacgtc  tacagtatct
tatgctgcaa  agaaagttcc  gatcccagca  gttataacag  cagtgggcag  ttgatggcaa
gtaaaatgga  tacctgctct  agtaacctga  ataacagcat  atacaaaaag  ctgttaactt
aggaaaaggg  actgctggga  ggttaaaaag  aaaagtttat  aaaagtgaat  aacctgagga
ttctattagt  ccccacccaa  actttattga  ttcacctcct  aaaacaacag  atgtacgact
tgcataccctg  ctttttatgg  gagctgtcaa  gcatgtattt  ttgtcaatta  ccagaaagat
aacaggacga  gatgacggtg  ttattccaag  ggaatattgc  caatgctaca  gtaataaatg
aatgtcactt  ctggatatag  ctaggtgaca  tatacatact  tacatgtgtg  tatatgtaga
tgtatgcaca  cacatatatt  atttgcagtg  cagtatagaa  taggcacttt  aaaacactct
ttccccgcac  cccagcaatt  atgaaaataa  tctctgattc  cctgatttaa  tatgcaaagt
ctaggttggt  agagtttagc  cctgaacatt  tcatggtgtt  catcaacagt  gagagactcc
```

Fig. 5 - Continued

```
atagtttggg cttgtaccac ttttgcaaat aagtgtattt tgaaattgtt tgacggcaag
gtttaagtta ttaagaggta agacttagta ctatctgtgc gtagaagttc tagtgtttc
aattttaaac atatccaagt ttgaattcct aaaattatgg aaacagatga aaagcctctg
ttttgatatg ggtagtattt tttacatttt acacactgta cacataagcc aaaactgagc
ataagtcctc tagtgaatgt aggctggctt tcagagtagg ctattcctga gagctgcatg
tgtccgcccc cgatggagga ctccaggcag cagacacatg ccagggccat gtcagacaca
gattggccag aaaccttcct gctgagcctc acagcagtga gactggggcc actacatttg
ctccatcctc ctgggattgg ctgtgaactg atcatgttta tgagaaactg gcaaagcaga
atgtgatatc ctaggaggta atgaccatga aagacttctc tacccatctt aaaaacaacg
aaagaaggca tggacttctg gatgcccatc cactgggtgt aaacacatct agtagttgtt
ctgaaatgtc agttctgata tggaagcacc cattatgcgc tgtggccact ccaataggtg
ctgagtgtac agagtggaat aagacagaga cctgccctca gagcaaagt agatcatgca
tagagtgtga tgtatgtgta ataaatatgt tcacacaaa caaggcctgt cagctaaaga
agtttgaaca tttgggttac tatttcttgt ggttataact taatgaaaac aatgcagtac
aggacatata ttttttaaaa taagtctgat ttaattgggc actatttatt tacaaatgtt
ttgctcaata gattgctcaa atcaggtttt cttttaagaa tcaatcatgt cagtctgctt
agaaataaca gaagaaaata gaattgacat tgaaatctag gaaaattatt ctataatttc
catttactta agacttaatg agactttaaa agcatttttt aacctcctaa gtatcaagta
tagaaaatct tcatggaatt cacaaagtaa tttggaaatt aggttgaaac atatctctta
tcttacgaaa aaatggtagc attttaaaca aaatagaaag ttgcaaggca aatgtttatt
taaagagca ggccaggcgc ggtggctcac gcctgtaatc ccagcacttt gggaggctga
ggcgggtgga tcacgaggtc aggagatcga gaccatcctg gctaacacgg tgaaacccgt
ctctactaaa aatgcaaaaa aaattagccg ggcgtggtgg caggcacctg tagtcccagc
tactcgggag gctgaggcag gagactggcg tgaacccagg aggcggacct tgtagtgagc
cgagatcgcg ccactgtgct ccagcctggg caacagagca agactccatc tc
```

Fig. 6

```
ggcgggggc gcacagagcc agaggggctt gcgagcggcg gctgagggac cgcggggagg
gggcgccgag cggctccagc gcagagactc tcactgcacg ccggaggccc cttcctcgct
ccgccgcgc gacgcgcgc cccagtcccg ccccgcccg ctaaccgccc cagacacagc
gctgccgag ggtgcttgg acctgatct tacccgtggg cacctgcgc tctgcctgcc
gcgaagaccg gctcccgac ccgcagaagt caggagagag ggtgaagcgg agcagcccga
ggcggggcag cctcccggag cagcgccgcg cagagcccgg gacaatgggg ccgcggcggc
tgctgctggt ggccgcctgc ttcagtctgt gcggccgct gttgtctgcc cgcaccgggg
cccgcaggcc agaatcaaaa gcaacaaatg ccaccttaga tccccggtca tttcttctca
ggaaccccaa tgataaatat gaaccatttt gggaggatga ggagaaaaat gaaagtgggt
```

Figure 6 - Continued

```
taactgaata cagattagtc tccatcaata aaagcagtcc tcttcaaaaa caacttcctg
cattcatctc agaagatgcc tccggatatt tgaccagctc ctggctgaca ctctttgtcc
catctgtgta cacggagtg tttgtagtca gcctcccact aaacatcatg gccatcgttg
tgttcatcct gaaaatgaag gtcaagaagc cggcggtggt gtacatgctg cacctggcca
cggcagatgt gctgtttgtg tctgtgctcc cctttaagat cagctattac ttttccggca
gtgattggca gtttgggtct gaattgtgtc gcttcgtcac tgcagcattt tactgtaaca
tgtacgcctc tatcttgctc atgacagtca taagcattga ccggtttctg gctgtggtgt
atcccatgca gtccctctcc tggcgtactc tgggaagggc ttccttcact tgtctggcca
tctggctttt ggccatcgca ggggtagtgc ctctcgtcct caaggagcaa accatccagg
tgcccgggct caacatcact acctgtcatg atgtgctcaa tgaaaccctg ctcgaaggct
actatgccta ctacttctca gccttctctg ctgtcttctt ttttgtgccg ctgatcattt
ccacggtctg ttatgtgtct atcattcgat gtcttagctc ttccgcagtt gccaaccgca
gcaagaagtc ccgggctttg ttcctgtcag ctgctgtttt ctgcatcttc atcatttgct
tcggacccac aaacgtcctc ctgattgcgc attactcatt cctttctcac acttccacca
cagaggctgc ctactttgcc tacctcctct gtgtctgtgt cagcagcata agctcgtgca
tcgaccccct aatttactat tacgcttcct ctgagtgcca gaggtacgtc tacagtatct
tatgctgcaa agaaagttcc gatccagca gttataacag cagtgggcag ttgatggcaa
gtaaaatgga tacctgctct agtaacctga ataacagcat atacaaaaag ctgttaactt
aggaaaaggg actgctggga ggttaaaaag aaaagtttat aaaagtgaat aacctgagga
ttctattagt ccccacccaa actttattga ttccctcct aaaacaacag atgtacgact
tgcatacctg ctttttatgg gagctgtcaa gcatgtattt ttgtcaatta ccagaaagat
aacaggacga gatgacggtg ttattccaag ggaatattgc caatgctaca gtaataaatg
aagtcacttt ctggatatag ctaggtgaca tatacatact tacatgtgtg tatatgtaga
tgtatgcaca cacatatatt atttgcagtg cagtatagaa taggcacttt aaaacactct
ttccccgcac cccagcaatt atgaaaataa tctctgattc cctgatttaa tatgcaaagt
ctaggttggt agagtttagc cctgaacatt tcatggtgtt catcaacagt gagagactcc
atagtttggg cttgtaccac ttttgcaaat aagtgtattt tgaaattgtt tgacggcaag
gtttaagtta ttaagaggta agacttagta ctatctgtgc gtagaagttc tagtgttttc
aatttaaaac atatccaagt ttgaattcct aaaattatgg aaacagatga aaagcctctg
ttttgatatg ggtagtattt tttacatttt acacactgta cacataagcc aaaactgagc
ataagtcctc tagtgaatgt aggctggctt tcagagtagg ctattcctga gagctgcatg
tgtccgcccc cgatggagga ctccaggcag cagacacatg ccagggccat gtcagacaca
gattggccag aaaccttcct gctgagcctc acagcagtga gactggggcc actacattg
ctccatcctc ctgggattgg ctgtgaactg atcatgttta tgagaaactg gcaaagcaga
atgtgatatc ctaggaggta atgaccatga aagacttctc tacccatctt aaaaacaacg
aaagaaggca tggacttctg gatgcccatc cactgggtgt aaacacatct agtagttgtt
ctgaaatgtc agttctgata tggaagcacc cattatgcgc tgtggccact ccaataggtg
```

Fig. 6 - Continued

```
ctgagtgtac agagtggaat aagacagaga cctgccctca agagcaaagt agatcatgca
tagagtgtga tgtatgtgta ataaatatgt ttcacacaaa caaggcctgt cagctaaaga
agtttgaaca tttgggttac tatttcttgt ggttataact taatgaaaac aatgcagtac
aggacatata ttttttaaaa taagtctgat ttaattgggc actatttatt tacaaatgtt
ttgctcaata gattgctcaa atcaggtttt cttttaagaa tcaatcatgt cagtctgctt
agaaataaca gaagaaaata gaattgacac tgaaatctag gaaaattatt ctataatttc
cattacttta agcttaatg agactttaaa agcatttttt aacctcctaa gtatcaagta
tagaaaatct tcatggaatt cacaaagtaa tttggaaatt aggttgaaac atatctctta
tcttacgaaa aaatggtagc attttaaaca aaatagaaag ttgcaaggca aatgtttatt
taaagagca ggccaggcgc ggtggctcac gcctgtaatc ccagcacttt gggaggctga
ggcgggtgga tcacgaggtc aggagatcga gaccatcctg gctaacacgg tgaaaccccgt
ctctactaaa aatgcaaaaa aaattagccg ggcgtggtgg caggcacctg tagtcccagc
tactcgggag gctgaggcag gagactggcg tgaacccagg aggcggacct tgtagtgagc
cgagatcgcg ccactgtgct ccagcctggg caacagagca agactccatc tc
```

Fig. 7

```
ggcgggggc gcacagagcc agagggctt gcgagcggcg gctgagggac cgcggggagg
gggcgccgag cggctccagc gcagagactc tcactgcacg ccggaggccc cttcctcgct
ccgccgcgc gaccgcgcgc cccagtcccg ccccgcccg ctaaccgccc cagacacagc
gctcgccgag ggtcgcttgg accctgatct tacccgtggg caccctgcgc tctgcctgcc
gcgaagaccg gctccccgac ccgcagaagt caggagagag ggtgaagcgg agcagcccga
ggcggggcag cctcccggag cagcgccgcg cagagcccgg gacaatgggg ccgcggcggc
tgctgctggt ggccgcctgc ttcagtctgt gcgggccgct gttgtctgcc cgcacccggg
cccgcaggcc agaatcaaaa gcaacaaatg ccaccttaga tccccggtca tttcttctca
ggaacccaa tgataaatat gaaccatttt gggaggatga ggagaaaaat gaaagtgggt
taactgaata cagattagtc tccatcaata aaagcagtcc tcttcaaaaa caacttcctg
cattcatctc agaagatgcc tccggatatt tgaccagctc ctggctgaca ctctttgtcc
catctgtgta caccggagtg tttgtagtca gcctcccact aaacatcatg gccatcgttg
tgttcatcct gaaaatgaag gtcaagaagc cggcggtggt gtacatgctg cacctggcca
cggcagatgt gctgtttgtg tctgtgctcc cctttaagat cagctattac tttccggca
gtgattggca gtttgggtct gaattgtgtc gcttcgtcac tgcagcattt tactgtaaca
tgtacgcctc tatcttgctc atgacagtca taagcattga ccggtttctg gctgtggtgt
atccatgca gtccctctcc tggcgtactc tgggaagggc ttccttcact tgtctggcca
tctgggcttt ggccatcgca gggtagtgc ctctcgtcct caaggagcaa accatccagg
tgccgggct caacatcact acctgtcatg atgtgctcaa tgaaaccctg ctcgaaggct
```

Fig. 7 - Continued

```
actatgccta ctacttctca gccttctctg ctgtcttctt ttttgtgccg ctgatcattt
ccacggtctg ttatgtgtct atcattcgat gtcttagctc ttccgcagtt gccaaccgca
gcaagaagtc ccgggctttg ttcctgtcag ctgctgtttt ctgcatcttc atcatttgct
tcggacccac aaacgtcctc ctgattgcgc attactcatt cctttctcac acttccacca
cagaggctgc ctactttgcc tacctcctct gtgtctgtgt cagcagcata agctcgtgca
tcgacccct aatttactat tacgcttcct ctgagtgcca gaggtacgtc tacagtatct
tatgctgcaa agaaagttcc gatcccagca gttataacag cagtgggcag ttgatggcaa
gtaaaatgga tacctgctct agtaacctga ataacagcat atacaaaaag ctgttaactt
aggaaaggg actgctggga ggttaaaaag aaaagtttat aaaagtgaat aacctgagga
ttctattagt ccccacccaa actttattga ttcacctcct aaaacaacag atgtacgact
tgcatacctg ctttttatgg gagctgtcaa gcatgtattt tgtcaatta ccagaaagat
aacaggacga gatgacggtg ttattccaag ggaatattgc caatgctaca gtaataaatg
aatgtcactt ctggatatag ctaggtgaca tatacatact tacatgtgtg tatatgtaga
tgtatgcaca cacatatatt atttgcagtg cagtatagaa taggcactt aaaacactct
ttccccgcac cccagcaatt atgaaaataa tctctgattc cctgatttaa tatgcaaagt
ctaggttggt agagtttagc cctgaacatt tcatggtgtt catcaacagt gagagactcc
atagtttggg cttgtaccac ttttgcaaat aagtgtattt tgaaattgtt tgacggcaag
gtttaagtta ttaagaggta agacttagta ctatctgtgc gtagaagttc tagtgttttc
aattttaaac atatccaagt ttgaattcct aaaattatgg aaacagatga aaagcctctg
ttttgatatg ggtagtattt tttacatttt acacactgta cacataagcc aaaactgagc
ataagtcctc tagtgaatgt aggctggctt tcagagtagg ctattcctga gagctgcatg
tgtccgcccc cgatggagga ctccaggcag cagacacatg ccagggccat gtcagacaca
gattggccag aaaccttcct gctgagcctc acagcagtga gactggggcc actacatttg
ctccatcctc ctgggattgg ctgtgaactg atcatgttta tgagaaactg gcaaagcaga
atgtgatatc ctaggaggta atgaccatga aagacttctc tacccatctt aaaaacaacg
aaagaaggca tggacttctg gatgcccatc cactgggtgt aaacacatct agtagttgtt
ctgaaatgcc agttctgata tggaagcacc cattatgcgc tgtggccact ccaataggtg
ctgagtgtac agagtggaat aagacagaga cctgccctca agagcaaagt agatcatgca
tagagtgtga tgtatgtgta ataaatatgt ttcacacaaa caaggcctgt cagctaaaga
agtttgaaca tttggttac tatttcttgt ggttataact taatgaaaac aatgcagtac
aggacatata ttttttaaaa taagtctgat ttaattgggc actatttatt tacaaatgtt
ttgctcaata gattgctcaa atcaggtttt cttttaagaa tcaatcatgt cagtctgctt
agaaataaca gaagaaaata gaattgacat tgaaatctag gaaaattatt ctataatttc
catttactta agacttaatg agactttaaa agcatttttt aacctcctaa gtatcaagta
tagaaaatct tcatggaatt cacaaagtaa ttggaaatt aggttgaaac atatctctta
tcttacgaaa aaatggtagc attttaaaca aaatagaaag ttgcaaggca aatgtttatt
taaaagagca ggccaggcgc ggtggctccc gcctgtaatc ccagcacttt gggaggctga
```

Fig. 7 - Continued

```
ggcgggtgga tcacgaggtc aggagatcga ccatcctg gctaacacgg tgaaaccgt
ctctactaaa aatgcaaaaa aaattagccg ggcgtggtgg caggcacctg tagtcccagc
tactcgggag gctgaggcag gagactggcg tgaacccagg aggcggacct tgtagtgagc
cgagatcgcg ccactgtgct ccagcctggg caacagagca agactccatc tc
```

Fig. 8

```
ggcggggggc gcacagagcc agagggcttt gcgagcggcg gctgagggac cgcggggagg
gggcgccgag cggctccagc gcagagactc tcactgcacg ccggaggccc cttcctcgct
ccgcccgcgc gaccgcgcgc cccagtcccg cccgccccg ctaaccgccc cagacacagc
gctcgccgag ggtcgcttgg accctgatct tacccgtggg caccctgcgc tctgcctgcc
gcgaagaccg gctccccgac ccgcagaagt caggagagag ggtgaagcgg agcagcccga
ggcggggcag cctcccggag cagcgccgcg cagagccggg acaatggggg ccgcggcggc
tgctgctggt ggccgcctgc ttcagtctgt gcggcccgct gttgtctgcc cgcacccggg
cccgcaggcc agaatcaaaa gcaacaaatg ccacttaga tccccggtca tttcttctca
ggaaccccaa tgataaatat gaaccatttt gggaggatga ggagaaaaat gaaagtgggt
taactgaata cagattagtc tccatcaata aaagcagtcc tcttcaaaaa caacttcctg
cattcatctc agaagatgcc tccggatatt tgaccagctc ctggctgaca ctctttgtcc
catctgtgta caccggagtg tttgtagtca gcctcccact aaacatcatg gccatcgttg
tgttcatcct gaaaatgaag gtcaagaagc cggcggtggt gtacatgctg cacctggcca
cggcagatgt gtgtttgtg tctgtgctcc cctttaagat cagctattac ttttccggca
gtgattggca gtttgggtct gaattgtgtc gcttcgtcac tgcagcattt tactgtaaca
tgtacgcctc tatcttgctc atgacagtca taagcattga ccggtttctg gctgtggtgt
atcccatgca gtccctctcc tggcgtactc tgggaagggc ttccttcact tgtctggcca
tctgggcttt ggccatcgca ggggtagtgc ctctcgtcct caaggagcaa accatccagg
tgcccgggct caacatcact acctgtcatg atgtgctcaa tgaaaccctg ctcgaaggct
actatgccta ctacttctca gccttctctg ctgtcttctt ttttgtgccg ctgatcattt
ccacggtctg ttatgtgtct atcattcgat gtcttagctc ttccgcagtt gccaaccgca
gcaagaagtc ccgggctttg ttcctgtcag ctgctgtttt ctgcatcttc atcatttgct
tggacccac aaacgtcctc ctgattgcgc attactcatt cctttctcac acttccacca
cagaggctgc ctactttgcc tacctcctct gtgtctgtgt cagcagcata gctcgtgca
tgacccct aatttactat tacgcttcct ctgagtgcca gaggtacgtc tacagtatct
tatgctgcaa agaaagttcc gatcccagca gttataacag cagtgggcag ttgatggcaa
gtaaaatgga tacctgtctct agtaacctga ataacagcat atacaaaaag ctgttaactt
aggaaaaggg actgctggga ggttaaaaag aaagtttat aaaagtgaat aacctgagga
ttctattagt cccacccaa actttattga ttcacctcct aaaacaacag atgtacgact
```

Fig. 8 - Continued

```
tgcatacctg ctttttatgg gagctgtcaa gcatgtattt ttgtcaatta ccagaaagat
aacaggacga gatgacggtg ttattccaag ggaatattgc caatgctaca gtaataaatg
aatgtcactt ctggatatag ctaggtgaca tatacatact tacatgtgtg tatatgtaga
tgtatgcaca cacatatatt atttgcagtg cagtatagaa taggcacttt aaaacactct
ttccccgcac cccagcaatt atgaaaataa tctctgattc cctgatttaa tatgcaaagt
ctaggttggt agagtttagc cctgaacatt tcatggtgtt catcaacagt gagagactcc
atagtttggg cttgtaccac ttttgcaaat aagtgtattt tgaaattgtt tgacgcaag
gtttaagtta ttaagaggta agacttagta ctatctgtgc gtagaagttc tagtgttttc
aattttaaac atatccaagt ttgaattcct aaaattatgg aaacagatga aaagcctctg
ttttgatatg ggtagtattt tttacatttt acacactgta cacataagcc aaaactgagc
ataagtcctc tagtgaatgt aggctggctt tcagagtagg ctattcctga gagctgcatg
tgtccgcccc cgatggagga ctccaggcag cagacacatg ccagggccat gtcagacaca
gattggccag aaaccttcct gctgagcctc acagcagtga gactggggcc actacatttg
ctccatcctc ctgggattgg ctgtgaactg atcatgttta tgagaaactg gcaaagcaga
atgtgatatc ctaggaggta atgaccatga aagacttctc tacccatctt aaaaacaacg
aaagaaggca tggacttctg gatgcccatc cactgggtgt aaacacatct agtagttgtt
ctgaaatgtc agttctgata tggaagcacc cattatgcgc tgtggccact ccaataggtg
ctgagtgtac agagtggaat aagacagaga cctgccctca agagcaaagt agatcatgca
tagagtgtga tgtatgtgta ataaatatgt ttcacacaaa caaggcctgt cagctaaaga
agtttgaaca tttggttac tattccttgt ggttataact taatgaaaac aatgcagtac
aggacatata ttttttaaaa taagtctgat ttaattgggc actatttatt tacaaatgtt
ttgctcaata gattgctcaa atcaggtttt cttttaagaa tcaatcatgt cagtctgctt
agaaataaca gaagaaaata gaattgacac tgaaatctag gaaaattatt ctataattc
catttactta agacttaatg agactttaaa agcatttttt aacctcctaa gtatcaagta
tagaaaatct tcatggaatt cacaaagtaa tttggaaatt aggttgaaac atatctctta
tcttacgaaa aaatggtagc atttttaaaca aaatagaaag ttgcaaggca aatgtttatt
taaaagagca ggccaggcgc ggtggctccc gcctgtaatc ccagcacttt gggaggctga
ggcgggtgga tcacgaggtc aggagatcga gaccatcctg gctaacacgg tgaaaccccgt
ctctactaaa aatgcaaaaa aaattagccg ggcgtggtgg caggcacctg tagtcccagc
tactcgggag gctgaggcag gagactggcg tgaacccagg aggcggacct tgtagtgagc
cgagatcgcg ccactgtgct ccagcctggg caacagagca agactccatc tc
```

Fig. 9 ac agagtggaat aagacagaga cctgccctca agagcaaagt agatcatgca
tagagtgtga tgtatgtgta ataaatatgt ttcacacaaa caaggcctgt cagctaaaga
agtttgaaca tttgggttac tatttcttgt ggttataact taatgaaaac aatgcagtac
aggacatata ttttttaaaa taagtctgat ttaattgggc actatttatt tacaaatgtt
ttgctcaata gattgctcaa atcaggtttt cttttaagaa tcaatcatgt cagtctgctt
agaaataaca gaagaaaata gaattgacat tgaaatctag gaaaattatt ctataatttc
catttactta agacttaatg agactttaaa agcatttttt aacctcctaa gtatcaagta
tagaaaatct tcatggaatt cacaaagtaa tttggaaatt aggttgaaac atatctctta
tcttacgaaa aaatggtagc attttaaaca aaatagaaag ttgcaaggca aatgtttatt
taaaagagca ggccaggcgc ggtggctcac gcctgtaatc ccagcacttt gggaggctga
ggcgggtgga tcacgaggtc aggagatcga gaccatcctg gctaacacgg tgaaacccgt
ctctactaaa aatgcaaaaa aaattagccg ggcgtggtgg caggcacctg tagtcccagc
tactcgggag gctgaggcag gagactggcg tgaacccagg aggcggacct tgtagtgagc
cgagatcgcg ccactgtgct ccagcctggg caacagagca agactccatc tcaaaaaata
aaaataaata aaaataaaa aataaaaga gcaaactatt tccaaatacc atagaataac
ttacataaaa gtaatataac tgtattgtaa gtagaagcta gcactgg

Fig. 10 ac agagtggaat aagacagaga cctgccctca agagcaaagt agatcatgca
tagagtgtga tgtatgtgta ataaatatgt ttcacacaaa caaggcctgt cagctaaaga
agtttgaaca tttgggttac tatttcttgt ggttataact taatgaaaac aatgcagtac
aggacatata ttttttaaaa taagtctgat ttaattgggc actatttatt tacaaatgtt
ttgctcaata gattgctcaa atcaggtttt cttttaagaa tcaatcatgt cagtctgctt
agaaataaca gaagaaaata gaattgacac tgaaatctag gaaaattatt ctataatttc
catttactta agacttaatg agactttaaa agcatttttt aacctcctaa gtatcaagta
tagaaaatct tcatggaatt cacaaagtaa tttggaaatt aggttgaaac atatctctta
tcttacgaaa aaatggtagc attttaaaca aaatagaaag ttgcaaggca aatgtttatt
taaaagagca ggccaggcgc ggtggctcac gcctgtaatc ccagcacttt gggaggctga
ggcgggtgga tcacgaggtc aggagatcga gaccatcctg gctaacacgg tgaaacccgt
ctctactaaa aatgcaaaaa aaattagccg ggcgtggtgg caggcacctg tagtcccagc
tactcgggag gctgaggcag gagactggcg tgaacccagg aggcggacct tgtagtgagc
cgagatcgcg ccactgtgct ccagcctggg caacagagca agactccatc tcaaaaaata
aaaataaata aaaataaaa aataaaaga gcaaactatt tccaaatacc atagaataac
ttacataaaa gtaatataac tgtattgtaa gtagaagcta gcactgg

Fig. 11 ac agagtggaat aagacagaga cctgccctca agagcaaagt agatcatgca
tagagtgtga tgtatgtgta ataaatatgt ttcacacaaa caaggcctgt cagctaaaga
agtttgaaca tttgggttac tatttcttgt ggttataact taatgaaaac aatgcagtac
aggacatata ttttttaaaa taagtctgat ttaattgggc actatttatt tacaaatgtt
ttgctcaata gattgctcaa atcaggtttt cttttaagaa tcaatcatgt cagtctgctt
agaaataaca gaagaaaata gaattgacat tgaaatctag gaaaattatt ctataatttc
catttactta agacttaatg agactttaaa agcattttt aacctcctaa gtatcaagta
tagaaaatct tcatggaatt cacaaagtaa tttggaaatt aggttgaaac atatctctta
tcttacgaaa aaatggtagc attttaaaca aaatagaaag ttgcaaggca aatgtttatt
taaaagagca ggccaggcgc ggtggctccc gcctgtaatc ccagcactt gggaggctga
ggcgggtgga tcacgaggtc aggagatcga gaccatcctg gctaacacgg tgaaacccgt
ctctactaaa aatgcaaaaa aaattagccg ggcgtggtgg caggcacctg tagtcccagc
tactcgggag gctgaggcag gagactggcg tgaacccagg aggcggacct tgtagtgagc
cgagatcgcg ccactgtgct ccagcctggg caacagagca agactccatc tcaaaaaata
aaaataaata aaaataaaa aataaaga gcaaactatt tccaaatacc atagaataac
ttacataaaa gtaatataac tgtattgtaa gtagaagcta gcactgg

Fig. 12 ac agagtggaat aagacagaga cctgccctca agagcaaagt agatcatgca
tagagtgtga tgtatgtgta ataaatatgt ttcacacaaa caaggcctgt cagctaaaga
agtttgaaca tttgggttac tatttcttgt ggttataact taatgaaaac aatgcagtac
aggacatata ttttttaaaa taagtctgat ttaattgggc actatttatt tacaaatgtt
ttgctcaata gattgctcaa atcaggtttt cttttaagaa tcaatcatgt cagtctgctt
agaaataaca gaagaaaata gaattgacac tgaaatctag gaaaattatt ctataatttc
catttactta agacttaatg agactttaaa agcattttt aacctcctaa gtatcaagta
tagaaaatct tcatggaatt cacaaagtaa tttggaaatt aggttgaaac atatctctta
tcttacgaaa aaatggtagc attttaaaca aaatagaaag ttgcaaggca aatgtttatt
taaaagagca ggccaggcgc ggtggctccc gcctgtaatc ccagcactt gggaggctga
ggcgggtgga tcacgaggtc aggagatcga gaccatcctg gctaacacgg tgaaacccgt
ctctactaaa aatgcaaaaa aaattagccg ggcgtggtgg caggcacctg tagtcccagc
tactcgggag gctgaggcag gagactggcg tgaacccagg aggcggacct tgtagtgagc
cgagatcgcg ccactgtgct ccagcctggg caacagagca agactccatc tcaaaaaata Fig. 12 – Continued

```
aaaataaata aaaataaaa aaataaaaga gcaaactatt tccaaatacc atagaataac
ttacataaaa gtaatataac tgtattgtaa gtagaagcta gcactgg
```

Fig. 13

```
ggcgggggc gcacagagcc
```

Fig. 14

```
gagatggagt cttgctctgt tg
```

Fig. 15

```
acagagtgga ataagacaga g
```

Fig. 16

```
ccagtgctag cttctactta c
```

Fig. 17

```
MGPRRLLLVAACFSLCGPLLSARTRARRPESKATNATLDPRSFLLRNPNDKYEPFWED
EEKNESGLTEYRLVSINKSSPLQKQLPAFISEDASGYLTSSWLTLFVPSVYTGVFVVS
LPLNIMAIVVFILKMKVKKPAVVYMLHLATADVLFVSVLPFKISYYFSGSDWQFGSEL
CRFVTAAFYCNMYASILLMTVISIDRFLAVVYPMQSLSWRTLGRASFTCLAIWALAIA
GVVPLVLKEQTIQVPGLNITTCHDVLNETLLEGYYAYYFSAFSAVFFFVPLIISTVCY
VSIIRCLSSSAVANRSKKSRALFLSAAVFCIFIICFGPTNVLLIAHYSFLSHTSTTEA
AYFAYLLCVCVSSISSCIDPLIYYYASSECQRYVYSILCCKESSDPSSYNSSGQLMAS
KMDTCSSNLNNSIYKKLLT
```

ANALYSIS AND USE OF PAR1 POLYMORPHISMS FOR EVALUATING THE RISK OF CARDIOVASCULAR DISORDERS

FIELD OF THE INVENTION

The invention relates to polynucleotide sequences comprising genetic variations of the PAR1 gene at positions 3090 and/or 3329, and their use in determining a patient's risk of cardiovascular disorders.

BACKGROUND OF THE INVENTION

The protease-activated receptor 1 (PAR1) is a thrombin receptor which belongs to the class of G protein-coupled receptors (GCPR). The gene for PAR1 is located on chromosome 5q13, consists of two exons and covers a region of approx. 27 kb. PAR1 is expressed in, inter alia, endothelial cells, smooth muscles cells, fibroblasts, neurons and human platelets. In platelets, PAR1 is an important signal transduction receptor which is involved in the initiation of platelet aggregation.

PARs are activated via proteolytic removal of a part of the N terminus of said PARs, whereby a new N-terminal sequence is exposed which then activates the receptor.

PAR1 and PAR4 play a central part in the activation of platelets; the activation of these receptors in platelets leads to morphological changes, release of ADP and aggregation of said platelets.

A connection of coronary heart diseases with single nucleotide polymorphisms (SNP) in the promoter region of PAR1 in a group of Korean patients was not confirmed. In another study, a PAR1 promoter variant was shown to have a protective action for the development of venous thromboembolisms.

The sequence of the human PAR1 gene is known. The polynucleotide sequence of this gene can be accessed under the number NM-001992 at the NCBI nucleotide database. Likewise, the protein sequence is available under the number NP-001983 at the NCBI protein database. NCBI is the National Center for Biotechnology Information (postal address: National Center for Biotechnology Information, National Library of Medicine, Building 38A, Bethesda, Md. 20894, USA; Web address: www.ncbi.nhm.nih.gov). The cloning of the PAR1 gene has been described, inter alia, in "Schmidt et al., J. Biol. Chem. 271, 9307-9312, 1996".

DESCRIPTION OF THE INVENTION

There are various new polymorphisms of the PAR1 gene, by means of which it is possible to determine a relatively strong disposition of an individual for coronary heart diseases. The affected individuals are thus enabled to counteract this risk factor in time by adapting their life style accordingly, for example by compensating via increased control of other damaging influences such as smoking, alcohol consumption, cholesterol-rich food, high blood pressure etc.

Such health-related preventive mechanisms would not be possible without knowledge of the PAR1 polymorphisms which are explained in more detail below and the use thereof in corresponding methods.

Variants of a particular nucleotide sequence with substitutions at individual positions are known to the skilled worker under the term SNP (=single nucleotide polymorphism).

The invention relates to an isolated polynucleotide sequence of the PAR1 gene, which comprises a C for T substitution at position 3090 of the PAR1 sequence according to NM-001992 which, as prior art, is publicly available. In a preferred embodiment, the polynucleotide sequence of the PAR1 gene having a T to C substitution at position 3090 encompasses a sequence according to SEQ ID NO: 2 and, in a particularly preferred embodiment of said polynucleotide sequence, the latter comprises a sequence of SEQ ID NO: 2.

The invention furthermore relates to an isolated polynucleotide sequence of the PAR1 gene, which comprises an C for A substitution at position 3329 of the PAR1 sequence according to NM-001992 which, as prior art, is publicly available. In a preferred embodiment, the polynucleotide sequence of the PAR1 gene having an A to C substitution at position 3329 encompasses a sequence according to SEQ ID NO: 3 and, in a particularly preferred embodiment of said polynucleotide sequence, the latter comprises a sequence of SEQ ID NO: 3.

The invention also relates to an isolated polynucleotide sequence of the PAR1 gene, which comprises a C for T substitution at position 3090 of the PAR1 sequence according to NM-001992 and, simultaneously, a V for A substitution at position 3329 of said PAR1 sequence. In a preferred embodiment, the polynucleotide sequence of the PAR1 gene having a T to C substitution at position 3090 and a simultaneous A to C substitution at position 3329 encompasses a sequence according to SEQ ID NO: 4 and, in a particularly preferred embodiment of said polynucleotide sequence, the latter comprises a sequence of SEQ ID NO; 4.

The invention also relates to an isolated part of the polynucleotide sequence of the PAR1 gene, which comprises a sequence according to SEQ ID NO: 5.

The invention also relates to an isolated part of the polynucleotide sequence of the PAR1 gene, which sequence comprises a C for T substitution at position 3090, based on the PAR1 sequence according to NM-001992, which part comprises a sequence according to SED ID NO: 6.

The invention also relates to an isolated part of the polynucleotide sequence of the PAR1 gene, which sequence comprises a C for A substitution at position 3329, based on the PAR1 sequence according to NM-001992. which part comprises a sequence according to SED ID NO: 7.

The invention also relates to an isolated part of the polynucleotide sequence of the PAR1 gene, which sequence comprises a C for T substitution at position 3090, based on the PAR1 sequence according to NM-001992, and simultaneously a C for A substitution at position 3329 of said PAR1 sequence, which part comprises a sequence according to SEQ ID NO: 8.

The invention furthermore comprises the preparation of a 3592 base pair polynucleotide sequence of the PAR1 cDNA gene, which sequence may or may not comprise the polymorphisms at positions 3090 and 3329, as defined above, individually or in combination, which preparation comprises the following method steps:

a] Providing human cDNA comprising a PAR1 sequence according to SEQ ID NO: 2 and/or a PAR1 sequence according to SEQ ID NO: 3 and/or a PAR1 sequence according to SEQ ID NO: 4, b] Providing a primer pair having a sequence according to SEQ ID NO: 9 and SEQ ID NO: 10.

c] Amplifying the PAR1 polynucleotide sequence by the polymerase chain extension reaction (PCR), d] Isolating and/or purifying the 3.56 kb fragment obtained from c], e] Sequencing the fragment from d].

The invention also relates to the preparation of a polynucleotide sequence according to SEQ ID NO: 5, SEQ ID NO: 6, SEQ ID NO: 7 or SEQ ID NO: 8, which preparation comprises the following method steps:

a] Providing human genomic DNA comprising a PAR1 sequence according to SEQ ID NO: 1 and/or a PAR1 sequence according to SEQ ID NO: 2 and/or a PAR1 sequence according to SEQ ID NO: 3 and/or a PAR1 sequence according to SEQ ID NO: 4 b] Providing a primer pair according to SEQ ID NO: 11 and SEQ ID NO: 12 c] Amplifying the fragment of the PAR1 polynucleotide sequence by the polymerase chain extension reaction (PCR), d] Isolating and/or purifying the fragment obtained from c], e] Sequencing the fragment from d].

The invention furthermore relates to a method for detecting whether or not there is in a PAR1 gene a T to C substitution at position 3090 of the sequence according to NM-001992 and/or an A to C substitution at position 3329 of the sequence according to NM-001992, which method comprises the following method steps:

a] Providing biological material comprising human cells, b] Obtaining chromosomal DNA from the material of a], c] Amplifying a polynucleotide fragment by means of the primers according to SEQ ID NO: 11 and SEQ ID NO: 12, using a PCR reaction, d] Sequencing the polynucleotide fragment from c].

The invention furthermore relates to a method for detecting, whether or not there is in a PAR1 gene a T to C substitution at position 3090 of the sequence according to NM-001992 and/or an A to C substitution at position 3329 of the sequence according to NM-001992, which method comprises the following method steps:

a] Providing biological material comprising human cells, b] Obtaining RNA from the material of a], c] Transcribing said RNA to cDNA by means of reverse transcriptase, d] Possibly amplifying a polynucleotide fragment by means of the primers according to SEQ ID NO: 10 and SEQ ID NO: 11, using said PCR reaction, e] Sequencing the cDNA from c] and/or the polynucleotide fragment from d].

The invention also relates to a method for detecting whether or not there is in a PAR1 gene a T to C substitution at position 3090 of the sequence according to NM-001992 and/or an A to C substitution at position 3329 of the sequence according to NM-001992, which method comprises the following method steps:

a] Providing biological material comprising human cells, b] Obtaining chromosomal DNA from the material of a], c] Southern blotting the chromosomal DNA from b], d] Providing a probe according to SEQ ID NO: 5 and/or SEQ ID NO: 6 and/or SEQ ID NO: 7 and/or SEQ ID NO: 8, e] Hybridizing the Southern blot from c] with the probe form d] under stringent hybridization conditions, f] Determining the presence or absence of a genetic variation in the PAR1 gene at position 3090 and/or 3329 according to NM-001992 by comparing the results of the hybridization from e].

The invention furthermore relates to a method for detecting whether or not there is in a PAR1 gene a T to C substitution at position 3090 of the sequence according to NM-001992 and/or an A to C substitution at position 3329 of the sequence according to NM-001992, which method comprises the following method steps:

a] Providing biological material comprising human cells, b] Obtaining RNA from the material of a], c] Northern blotting the RNA from b], d] Providing a probe according to SEQ ID NO: 5 and/or SEQ ID NO: 6 and/or SEQ ID NO: 7 and/or SEQ ID NO: 8, e] Hybridizing the Northern blot form c] with the probe from d] under stringent hybridization conditions, f] Determining the presence or absence of a genetic variation in the PAR1 gene at position 3090 and/or 3329 according to NM-001992 by comparing the results of the hybridization.

Detection of the genetic variations or polymorphisms in the PAR1 gene at positions 3090 and/or 3329 may be used as (a) genetic marker for evaluating the risk of atrial fibrillation, acute coronary syndrome, cardiomyopathy and/or unstable angina, as (b) marker for preventive treatment for atrial fibrillation, acute coronary syndrome, cardiomyopathy and/or stable angina of the carriers of the corresponding genetic variants, as (c) marker for adjusting the dose of a pharmaceutically active substance to be administered for atrial fibrillation, acute coronary syndrome, cardiomyopathy and/or unstable angina, as (d) marker for determining the high throughput-screening strategy for identifying a pharmaceutically active substance for atrial fibrillation, acute coronary syndrome, cardiomyopathy and/or unstable angina, as (e) marker for identifying the relevant individuals or patients for clinic studies in order to test the tolerability, safety and efficacy of a pharmaceutical substance for atrial fibrillation, acute coronary syndrome, cardiomyopathy and/or unstable angina, and as (f) basis for developing assays systems for analyzing the genetic variation in the PAR1 gene at the DNA. RNA or protein level.

The invention also relates to an isolated polynucleotide sequence having from 21 to 50 nucleotides, which comprises a sequence according to SEQ ID NO: 11. Said sequence preferably comprises SEQ ID NO: 11. The invention furthermore relates to an isolated polynucleotide sequence having from 20 to 50 nucleotides, which comprises a sequence according to SEQ ID NO: 12. Said sequence preferably comprises SEQ ID NO: 12.

The invention also relates to the use of an isolated polynucleotide sequence having from 21 to 50 nucleotides, which encompasses or comprises a sequence according to SEQ ID NO: 11, in combination with an isolated polynucleotide sequence having from 20 to 50 nucleotides, which encompasses or comprises a sequence according to SEQ ID NO: 12, for amplifying a corresponding fragment of the PART1 gene by means of the polymerase chain extension reaction (PCR). This use preferably relates to the amplification of a fragment of a PAR1 gene having a T to C substitution at position 3090 of the sequence according to NM-001992 and/or having an A to C substitution at position 3329 of the sequence according to NM-001992.

Moreover, the invention comprises a kit of parts which comprises a] an isolated polynucleotide sequence of from 21 to 50 nucleotides in length, which encompasses or comprises a sequence according to SEQ ID NO: 11, b] an isolated polynucleotide sequence of from 20 to 50 nucleotides in length, which encompasses or comprises a sequence according to SEQ ID NO: 12, c] at least one enzyme for carrying out the polymerase chain extension reaction (PCR), d] possibly substances and/or solutions for carrying out the polymerase chain extension reaction, e] possibly polynucleotide sequences encompassing the PAR1 gene with or without substitution at position 3090 of the PAR1 sequence according to NM-001992 and/or position 3329 according to NM-001992 in full length and/or parts thereof f] and possibly reagents for carrying out the sequencing reaction.

Kit of parts here and below means the combination of said components which have been combined into a functional unit in spatial juxtaposition to each other.

The invention furthermore relates to the preparation of the above-described kit of parts, which comprises a] providing an isolated polynucleotide sequence of from 21 to 50 nucleotides in length, which encompasses or comprises a sequence according to SEQ ID NO: 11, b] providing an isolated polynucleotide sequence of from 20 to 50 nucleotides in length, which encompasses or comprises a sequence according to SEQ ID NO: 12, c] providing an enzyme for carrying out the polymerase chain extension reaction (PCR), d] providing, where appropriate, reagents for carrying out a sequencing e] possibly providing substances and/or solutions for carrying out said polymerase chain extension reaction (PCR)

f] possibly providing polynucleotide sequences comprising the PAR1 gene with or without a T to C substitution at position 3090 of the PAR1 sequence according to NM-001992 and/or an A to C substitution at position 3329 according to NM-001992, in each case in the full length, or parts thereof, g] introducing the components from a] to f] in each case separately into suitable containers, h] combining, where appropriate, the containers from g] in one or more pack units.

The above-described kit of parts may be used for amplifying a fragment of the PAR1 gene.

BRIEF DESCRIPTION OF THE FIGURES

FIG. 1 depicts the characteristics of the study group.

FIG. 2 depicts the distribution of PAR1 variants T3090C and A3329C in 1362 individuals analyzed.

FIG. 3 depicts the association of PAR1 variants C3090C with atrial fibrillation and cardiomyopathy.

FIG. 4 depicts the association of PAR1 variants C3329C with atrial fibrillation, acute coronary syndrome and unstable angina.

FIG. 5 depicts the polynucleotide sequence of the cDNA of the human PAR1 gene in 5'/3' orientation. The sequence corresponds to the sequence made publicly available by the NCBI Nucleotide Database under number NM-001992. The prepared sequence is identical to SEQ ID NO: 1.

FIG. 6 depicts the polynucleotide sequence of the cDNA of the human PAR1 gene in 5'/3' orientation with a polymorphism at position 3090 of the sequence according to NM-001992, which polymorphism comprises a T to C substitution. The depicted sequence is identical to SEQ ID NO: 2.

FIG. 7 depicts the polynucleotide sequence of the cDNA of the human PAR1 gene in 5'/3' orientation with a polymorphism at position 3329 of the sequence according to NM-001992, which polymorphism comprises an A to C substitution. The depicted sequence is identical to SEQ ID NO: 3.

FIG. 8 depicts the polynucleotide sequence of the cDNA of the human PAR1 gene in 5'/3' orientation with a polymorphism at position 3090 of the sequence according to NM-001992, which polymorphism comprises a T to C substitution, and with a simultaneous second polymorphism at position 3329 of the sequence according to NM-001992, which polymorphism comprises an A to C substitution. The depicted sequence is identical to SEQ ID NO: 4.

FIG. 9 depicts the polynucleotide sequence of a fragment of the human PAR1 gene in 5'/3' orientation. The depicted sequence is identical to SEQ ID NO: 5.

FIG. 10 depicts the polynucleotide sequence of a fragment of the human PAR1 gene in 5'/3' orientation with a polymorphism at position 3090 of the sequence according to NM-01992, which polymorphism comprises a T to C substitution. The depicted sequence is identical to SEQ ID NO: 6.

FIG. 11 depicts the polynucleotide sequence of a fragment of human PAR1 gene in 5'/3' orientation with a polymorphism at position 3329 of the sequence according to NM-001992, which polymorphism comprises an A to C substitution. The depicted sequence is identical to SEQ ID NO: 7.

FIG. 12 depicts the polynucleotide sequence of a fragment of the human PAR1 gene in 5'/3' orientation with a polymorphism at position 3090 of the sequence according to NM-001992, which polymorphism comprises a T to C substitution, and with a simultaneous second polymorphism at position 3329 of the sequence according to NM-001992, which polymorphism comprises an A to C substitution. The depicted sequence is identical to SEQ ID NO: 8.

FIG. 13 depicts the polynucleotide sequence in 5'/3' orientation of the 5' end of the cDNA of the human PAR1 gene. The depicted sequence is identical to SEQ ID NO: 9.

FIG. 14 depicts the polynucleotide sequence in 5'/3' orientation of the 3' end of the cDNA of the human PAR1 gene. The depicted sequence is identical to SEQ ID NO: 10.

FIG. 15 depicts the polynucleotide sequence in 5'/3' orientation of the cDNA of the human PAR1 gene, relating to positions 2767 to 2789 according to NM-001992. The depicted sequence is identical to SEQ ID NO: 11.

FIG. 16 depicts the polynucleotide sequence in 5'/3' orientation of the Exon No. 1 of the cDNA of the human PAR1 gene. The depicted sequence is identical to SEQ ID NO: 12.

FIG. 17 depicts the protein sequence of the human PAR1 receptor. The sequence corresponds to the sequence made publicly available by the NCBI Protein Database under number NP-001983. The depicted sequence is identical to SEQ ID NO: 13.

EXAMPLES

The technical aspects of the invention are discussed in more detail in the following embodiments.

Isolated polynucleotide sequences of the PAR1 gene may be prepared, for example, by amplification by means of the polymerase chain extension reaction (PCR). Suitable primers for this purpose are described in SEQ ID NO: 9 and SEQ ID NO: 10.

The PCR is an in-vitro technique which may be used to selectively duplicate polynucleotide sections which are flanked by two known sequences. Amplification requires short, single-stranded DNA molecules which are complementary to the ends of a defined sequence of a DNA or RNA template (primers). A DNA polymerase extends the primers, under the correct reaction conditions and in the presence of deoxynucleotide triphosphates (dNTPs), along the single-stranded and denatured polynucleotide template and thus synthesizes new DNA strands whose sequence is complementary to said template. During this process, the temperature is changed at regular intervals so that, time after time, the polynucleotide strands are denatured and the primers can be attached and extended. Heat-stable DNA polymerases, for example Taq polymerase, are used. A typical PCR reaction mixture contains, apart from a polynucleotide template, two suitable primer nucleotides, for example at concentrations between 0.2 to 2 µM, furthermore dNTPs, for example at concentrations of 200 µM per dNPT, furthermore $MgCl_2$ having a concentration of 1-2 mM, and 1-10 units of a heat-stable DNA polymerase such as, for example, Taq polymerase (*Thermus aquaticus* polymerase). Heat-stable DNA polymerase and the components for carrying out the same, and also protocols, are commercially supplied by numerous companies such as, for example, Roche Diagnostics, Clontech, Life Technologies, New England Biolabs, Promega, Stratagene, etc.

The polynucleotide template for amplifying the polynucleotide sequence to be isolated may be present in the form of RNA or DNA. If the polynucleotide template is RNA, then the latter is transcribed to DNA by means of reverse transcriptase, prior to the actual PCR reaction. The amount of polynucleotide template for carrying out the PCR reaction may be from 0.01 to 20 ng, for example.

The polynucleotide template is obtained using techniques known to the skilled worker for obtaining DNA and/or RNA from biological material. Biological material should include here, inter alia, the cells of a tissue or organ (e.g. brain, blood, liver, spleen, kidney, heart, blood vessels) of a vertebrate, including humans, or cells from a eukaryotic cell culture (e.g. Hela cells, CHO cells, 3T3 cells) or cells comprising bacteria or yeasts in which the DNA sequence to be isolated is present in cloned form.

Cells of a tissue assemblage or organ of a vertebrate, including humans, may be obtained by taking blood, tissue puncture or surgical techniques. A polynucleotide template may be obtained therefrom, for example, by disrupting the cells, possibly concentrating individual organelles, in particular the nucleus, and recovering the DNA or RNA by precipitation and centrifugation.

Another method for preparing isolated polynucleotide sequences of the PAR1 gene comprises cloning the PAR1 gene, subsequently expressing it in bacteria or yeast and purifying the expressed polynucleotide. The previously mentioned PCR reaction, for example, is suitable for preparing a polynucleotide fragment which is clonable. It is advantageous to use, for a fragment to be cloned, primers which carry the recognition sequence of a reaction enzyme 5' of the complementary sequence. The two primers may use in each case the same or different recognition sequences for restriction enzymes.

Examples of common restriction enzymes are: BamHI (GGATCC), ClaI (ATCGAT), EcoRI (GAATTC), EcoRV (GATATC), HindIII (AAGCTT) NcoI (CCATGG) SalI (GTCGAC), XbaI (TCTAG1).

For cloning, a vector is treated with the restriction enzymes which correspond to the recognition sequences attached to the primers. The fragment is connected to the vector by means of ligase by isolation and treatment with the same restriction enzymes. Vector means a DNA molecule such as, for example, a plasmid, bacteriophage or a cosmid, with the aid of which it is possible to clone genes or other DNA sequences and to introduce them into a bacterial or eukaryotic cell for replication. Examples of vectors are DNA molecules such as pBR322, pUC18/19, pBluescript, pcDNA3.1. Vectors are commercially available from specialist companies for biotechnological material, such as Roche Diagnostics, New England Biolabs, Promega, Stratagene etc.

The instructions required for carrying out the PCR reaction, for providing polynucleotides or for carrying out cloning procedures can be found by the skilled worker in the form of recipes and protocols in standard manuals such as, for example, in a] "Current Protocols in Molecular Biology by Frederick M. Ausubel (Editor), Roger Brent (Editor), Robert E. Kingston (Editor), David D. Moore (Editor), J. G. Seidman (Editor), Kevin Struhl (Editor), loose leaf edition, continuously updated, John Wiley & Sons, Inc., New York or in b] Short Protocols in Molecular Biology, 5th edition, by Frederick M. Ausubel (Editor), Roger Brent (Editor), Robert E. Kingston (Editor), David D. Moore (Editor), J. G. Seidman (Editor), John A. Smith (Editor), Kevin Struhl (Editor), October 2002, John Wiley & Sons, Inc., New York" or in c] "Molecular Cloning by J. Sambrock, E. F. Fritsch, T. Maniatis; Cold Spring Harbor Laboratory Press".

Suitable primer sequences are provided, for example, via chemical synthesis thereof which may be carried out commercially to order by companies such as MWG Biotech, etc.

Human cDNA from different organs is commercially available from companies such as, for example, Promega, Stratagene or others.

The sequencing of a polynucleotide is carried out by means of routine methods known to the skilled worker by using, for example, laboratory robots from companies such as, for example, Life Technologies/Applied Biosystems, BioRad or others.

Isolated polynucleotide sequences of the PAR1 variant and fragments therefrom may also be used for hybridization at different stringencies. Stringency describes reaction conditions which influence the specificity of hybridization or attachment of two single-stranded nucleic acid molecules. The stringency and thus also specificity of a reaction can be increased by increasing the temperature and lowering the ionic strength. Low stringency conditions are present, for example, if the hybridization is carried out at room temperature in 2×SSC solution. High stringency conditions are present, for example, if hybridization is carried out at 68° C. in 0.1×SSC/0.1% SDS solution.

Hybridization under stringent hybridization conditions in accordance with the present application means:

1] Hybridizing the labeled probe with the sample to be studied at 65° C. (or, in the case of oligonucleotides, 5° C. below the melting temperature) overnight in 50 mM Tris pH 7.5, 1NaCl, 1% SDS, 10% dextran sulfate, 0.5 mg/ml denatured salmon sperm DNA.
2] Washing at room temperature in 2×SSC for 10 min.
3] Washing at 65° C. (or, in the case of oligonucleotides, 5° C. below the melting temperature) in 1×SSC/1% SDS for 30 min.
4] Washing at 65° C. (or, in the case of oligonucleotides, 5° C. below the melting temperature) in 0.2×SSC/0.1% SDS for 30 min.
5] Washing at 65° C. (or, in the case of oligonucleotides, 5° C. below the melting temperature) in 0.1% SSC/0.1% SDS for 30 min.

DNA fragments of 20 nucleotides in overall length are to be regarded as being oligonucleotides for this purpose. The melting temperature results from the formula Tm=2 (number of A+T)+4 (number of G+C)C°.

A 2×SSC or 0.1×SSC solution is prepared by diluting a 20×SSC solution accordingly. The 20×SSC solution comprises a 3M NaCl/0.3 sodium citrate 2 $H_2O$ solution. SDS is sodium dodecyl sulfate.

The hybridization is carried out by transferring the polynucleotides to be studied to a nylon or nitrocellulose membrane (Southern blot—DNA; Northern blot—RNA), after electrophoretic fractionation and subsequent denaturation. The hybridization is carried out using a probe which is radiolabeled or has been labeled in another way, for example with the aid of fluorescent dyes. The probe comprises a usually single-stranded and/or denatured DNA or RNA polynucleotide sequence which binds to the complementary nucleotide sequence of the once again single-stranded and/or denatured DNA or RNA polynucleotide sequence to be studied.

Single nucleotide polymorphisms of the PAR1 gene may be detected with the aid of the primers of the invention, also by SSCP analysis. SSCP stands for Single Stranded Conformation Polymorphism which is an electrophoretic technique for identifying individual base pair substitutions. The polynucleotides to be studied are amplified by PCR by means of labeled primers and, after denaturation into single strands, fractionated in a polyacrylamide gel electrophoresis (PAGE). If the DNA fragments to be studied exhibit individual base pair substitutions, they then possess different conformations and thus migrate in the PAGE at different rates.

Examples of substances for carrying out the PCR are buffers such as Hepes or Tris, furthermore dAPP, dGTP, dTTP, dCTP, and $Mg^{2+}$ and possibly further divalent or monovalent irons. Solutions contain these substances in dissolved form.

Amplification of Genomic Regions of the PAR1 Gene

The T to C nucleotide substitution at position 3090 and the A to C substitution at position 3329 in the PAR1 sequence were detected using the following primers:

```
Primer 1:
5'-ACAGACTGGAATAAGACAGAG-3'     (SEQ ID NO: 11)

Primer 2:
5'-CCAGTGCTAGCTTCTACTTAC-3      (SEQ ID NO: 12)
```

Primer 1 (SEQ ID NO: 11) corresponds to positions 2767 to 2789 of the NM-001992 reference sequence. Primer 2 is derived from Exon No. 1 of the PAR1 gene.

PCR Protocol for the Amplification:

The reagents used are from Applied Biosystems (Foster City, USA): 20 ng of genomic DNA; 1 unit of TaqGold DNA polymerase; 1× Taq polymerase buffer; 500 µM of dNTPs; 2.5 mM $MgCl_2$: 200 nM of each amplification primer pair; $H_2O$ to 5 µl.

PCR Amplification Program for the Genotyping

| | |
|---|---|
| 95° C. for 10 min | x1 cycle |
| 95° C. for 30 sec | |
| 70° C. for 30 sec | x2 cycles |
| 95° C. for 30 sec | |
| 65° C. for 30 sec | x2 cycles; |
| 95° C. for 30 sec | |
| 60° C. for 30 | x2 cycles; |
| 95° C. for 30 sec | |
| 56° C. for 30 sec | |
| 72° C. for 30 sec | x40 cycles; |
| 72° C. for 10 min | |
| 4° C. for 30 sec | x1 cycle; |

Identification of SNPs

Protocol for the minisequencing and detection of the SNPs.

All reagents are from Applied Biosystems (Foster City, USA). 2 µl of purified PCR product, 1.5 µL of BigDye Terminator Kit, 200 nM sequencing primer; $H_2O$ to 10 µl.

Amplification Program for the Sequencing:

| | |
|---|---|
| 96° C. for 2 min | x1 cycle |
| 96° C. for 10 sec | |

| | |
|---|---|
| 55° C. for 10 sec | |
| 65° C. for 4 min | x30 cycles |
| 72° C. for 7 min | |
| 4° C. for 30 sec | x1 cycle; |

Analysis of the Sequencing Products:

The sequences were first analyzed using the sequence analysis software (Applied Biosystems, Foster City, USA) to obtain the raw data, then processed using Phred, Phrap, Polyphred and Consed. Phred, Phrap, Polyphred and Consed are software written by Phil Green at Washington University (http://www.genome.washington.edu).

Assigning PAR1 SNPs to Coronary Disorders

In a clinical study, two PAR1 polymorphisms from the 3'-noncoding region of the gene were studied for a connection with thrombotic and cardiovascular complications in a cohort of patients.

The following abbreviations are used below (all positions indicated refer to the nucleotide positions in the reference sequence NM-001992).

PAR1 T3090T describes the group of individuals whose alleles of the PAR1 gene both have a thymidine (T) at position 3090. These individuals are homozygous with respect to this PAR1 variant.

PAR1 T3090C describes the group of individuals whose one allele of the PAR1 gene has a cytidine (C) at position 3090 and whose other allele of the PAR1 gene has a thymidine (T) at position 3090. These individuals are heterozygous with respect to this PAR1 variant.

PAR1 C3090C describes the group of individuals whose alleles of the PAR1 gene both have a cytidine (C) at position 3090. These individuals are homozygous with respect to this PAR1 variant.

PAR1 A3329A describes the group of individuals whose alleles of the PAR1 gene both have an adenosine (A) at position 3329. These individuals are homozygous with respect to this PAR1 variant.

PAR1 A3329C describes the group of individuals whose one allele of the PAR1 gene has a cytidine (C) at position 3329 and whose other allele of the PAR1 gene has an adenosine (A) at position 3329. These individuals are heterozygous with respect to this PAR1 variant.

PAR1 C3329C describes the group of individuals whose alleles of the PAR1 gene both have a cytidine (C) at position 3329. These individuals are homozygous with respect to this PAR1 variant.

In the group of patients analyzed (FIG. 1), statistically significant associations of the homozygous carriers of the PAR1 variant C3090C with atrial fibrillation and cardiomyopathy were observed. After carrying out a logistic regression, a 1.97 fold increased risk of atrial fibrillation and a 1.84 fold increased risk of cardiomyopathy were found in homozygous carriers of the PAR1 variant C3090C compared to carriers of the PAR1 variants T3090/T3090T (FIG. 3).

It was shown that, for carriers of the PAR1 variant C3329C, said variant is associated with a 2.35 fold increased risk of atrial fibrillation compared to carriers of the PAR1 variants C3329A/A3329A. In carriers of the PAR1 variant C3329C, said variant seems, in addition, to be protective with respect to the appearance of acute coronary syndrome and unstable angina. Carriers of the PAR1 variant C3329C have a 2.78 fold reduced risk of the appearance of acute coronary syndrome and/or unstable angina compared to carriers of the PAR1 variants A3329C/A3329A (FIG. 4).

It is therefore possible, by means of a method of the invention and using an isolated PAR1 sequence of the particular SNP type or a fragment thereof, to determine for human individuals whether there is as assignment a risk group in accordance with the results presented.

Preparation of Plasmid DNA 1 ml of a bacterial overnight culture is transferred to an Eppendorf tube and centrifuged (5 000 rpm for 5 min) in a Heraeus Biofuge. The bacterial cell pellet is to be resuspended in 100 µl of cooled solution I and then to be placed on ice for 5 min.

Solution I: 25 mM tris-HCl, pH 8.0, 50 mM Glucose (Sterile-Filtered) 10 mM EDTA 100 µg/ml Rnase A.

After addition of 200 µl of solution II, the entire mixture is mixed well, resulting in alkaline denaturation of the DNA.

Solution II: 200 mM NaOH, 1% SDS.

After subsequent incubation for 5 min on ice, 150 µl of solution III are added to the mixture. This is followed by mixing once more and incubating on ice for a further 15 min.

Solution III: 3 M Sodium Acetate (pH 4.8).

Centrifugation in the Heraeus Biofuge at 12 000 rpm for 15 minutes removes the cell debris, the genomic DNA and the denatured proteins. The supernatant produced, which contains the plasmid DNA, is decanted into a second Eppendorf tube and admixed with 1 ml of 96% strength EtOH (or 300 µl of isopropanol). The precipitation mixture is mixed thoroughly and again centrifuged (15 min at 12 000 rpm in Heraeus Biofuge). This results in precipitation of the plasmid DNA. The plasmid DNA sediment is washed with ice-cold 70% strength EtOH and then dried in air. Finally, the dry sediment is taken up in 50 µl of sterile distilled water.

Alcohol Precipitation of DNA

Precipitation mixture: DNA solution, 1/10 volume of 3 M sodium acetate (pH 5.4), 2 to 3 volumes of 96% EtOH (1 volume of isopropanol).

The mixture is mixed well and can be stored at −20° C., although this does not increase the precipitation yield. The plasmid DNA is sedimented by centrifugation at 12 000 rpm for 20 minutes.

In order to remove residues of the sodium acetate used, the plasmid DNA must be washed once more with 1 ml of 70% strength EtOH after precipitation.

Phenol Extraction of DNA

A DNA solution is admixed with the same volume of phenol (Rotiphenol®, equilibrated with TE buffer, pH 7.6, Roth, Karlsruhe, Germany), shaken for 5 min and centrifuged at 5000 rpm. Most of the now denatured proteins accumulate in the interface. The upper, aqueous phase contains the DNA and is carefully removed by suction, and then mixed with a chloroform/isoamyl alcohol mixture (24:1) in order to remove phenol residues. This is followed by another centrifugation, after which the aqueous supernatant is removed and the DNA is isolated from the solution by alcohol precipitation.

Purification of Amplified DNA Molecules

DNA amplicons are purified using a PCR purification kit (Qiagen). This removes the starter molecules, nucleotides (dNTPs), polymerases and salts. For this purpose, the PCR reaction mixture is admixed with five times the volume of PB buffer, mixed well and applied to the Qiaquick column. The amplified DNA is then selectively bound to the column material, and the dNPTs are removed by washing twice with 750 µl of PE buffer. The amplified DNA is then eluted with the desired volume of water, with the best volume being the same as that of the PCR reaction mixture starting material.

DNA Cleavage with Restriction Enzymes

Mix: 3 µl of DNA, 2 µl of 10× cleavage buffer, 2.5-5 U of restriction enzyme (e.g. EcoRI, BamHI, SalI, XbaI, XhoI etc.), add distilled water to a volume of 20 µl.

Depending on the restriction enzyme, the cleavage reaction runs at 25-55° C. for 1-2 h. For analysis, the fragments are electrophoretically fractionated in an agarose or polyacrylamide gel in parallel with a length standard. If the reaction is a double cleavage, then first one enzyme is added to the mixture. After 1 hour, an aliquot is applied to an appropriate gel, and, if the cleavage has occurred, the second enzyme can be added. If the second enzyme does not cleave in the same cleavage buffer, then an alcohol precipitation is required first.

Agarose Gel Electrophoresis of DNA

The agarose (Roth) is dissolved in 1× agarose buffer at the desired concentration and boiled in a microwave oven, until the agarose has completely dissolved. The solution is then poured into a sealed Plexiglass flat bed gel chamber.

The DNA samples are admixed with 1/10 volume of loading blue (50% v/v glycerol; 50 mM EDTA; 0.005% w/v BPB [Merck, Darmstadt, Germany] and 0.005% xylene cyanol) and pipetted into the gel pockets which are generated by means of a comb.

The electrophoresis is carried out horizontally in 1× agarose buffer as running buffer at a constant voltage of 80-140 V, depending on the size of the gel and the distance between the electrodes.

1× agarose buffer: 40 mM Tris-HCl (pH 7.8), 5 mM sodium acetate, 1 mM EDTA.

Polyacrylamide Gel Electrophoresis of DNA 7.5% polyacrylamide gel solution; 0.94 ml of 40% strength acrylamide-bisacrylamide stock solution, 0.5 ml of 10×TBE buffer (400 mM Tris-HCl, pH 8.3; 200 mM sodium acetate, 20 mM EDTA), 0.25 ml of 1% AMPS, 10 µl of TEMED, 3.33 ml of distilled water.

This mixture is poured between well-cleaned, vertical glass plates mounted in vertical apparatuses for polymerization (approx. 10-20 min). The gel is run in 1×TBE buffer at a constant voltage of 104 V.

DNA Sequencing 1-2 µg of DNA are to be dissolved in 81 µl of distilled $H_2O$ and 9 µl of NaOH (2 N) is to be added for denaturation. After incubation at room temperature for 10 minutes, the mixture is precipitated, with thorough washing of the resulting DNA sediment with ice-cold 80% strength ethanol being important for the subsequent sequencing reactions. 2 µl of 5× Sequenase buffer (200 mM Tris-Cl pH 7.5/100 mM $MgCl_2$/250 mM NaCl), 1 µl of oligonucleotide (1 µM/µl) and, finally, distilled $H_2O$ are to be added to the sediment to a total volume of 10 µl. During the subsequent incubation in a 37° C. water bath for 30 minutes, the starter oligonucleotide hybridizes to the DNA.

Reagents added to the hybridization mixture for the sequencing reaction: 1.0 µl of DTT (0.1 M), 2.0 µl of labeling mixture (diluted 1:5), 0.5 µl of [α-$^{35}$S]dATP, 2 µl of Sequenase™ (13 U/µl, United States Biochemical), (diluted 1:8 with enzyme dilution buffer).

During the subsequent incubation at room temperature for 5 minutes, the counter strand is synthesized, with the synthetic DNA being labeled by incorporation of the radiolabeled dATP. This is followed by adding in each case 3.5 µl of the labeling mixture to 2.5 μl of the four different termination mixtures. Another incubation at 37° C. for 5 minutes results in the randomly distributed termination reactions of counter stand synthesis. The reactions are stopped by adding 4 μl of stop buffer, after which the mixtures are denatured at 80-90° C. and then applied to a 6% strength denatured sequencing gel. After loading the samples, the main run is carried out at 30-50 V and, respectively, 1300-1600 V for 2-5 h. The gel is then fixed in a 10% strength acetic acid bath (15 min), freed of urea residues under running water and then dried (for 45 min, using a heat gun, or for 2 h, in a 70° C. incubator). The subsequent autoradiography is carried out at 4° C. for 16-24 h (Fuji Medical X-ray-Film RX, 30×40; Kodak Scientific Imaging Film X-omat AR).

Labeling-mixture stock solution: in each case 7.5 μM dATP, dTTP, dGTP, dCTP

Termination mixtures: in each case 80 μM dATP, dTTP, dGTP, dCTP and in each case 8 μM of the respective ddNTP Sequenase dilution buffer: 10 mM Tris/HCl; pH 7.5, 5 mM DTT, 0.5 mg/ml BSA Stop buffer: 95% formamide, 20 mM EDTA, 0.005% (w/v) xylene cyanol FF Automated DNA Sequencing Mix: 1 μg of plasmid DNA (in the case of PCR fragments, for example, 100 ng/500 nucleotides), 3-5 pmol of starter molecule (PCR primer, Tm of 55° C., if possible), 4 μl of Dye Terminator ready-mix (FddNTPs-Ampli-TaqFS mixture), add distilled water to a volume of 20 μl.

The PCR reaction [25×(15 sec at 94° C., 15 sec. at 50° C., 4 min at 60° C. is precipitated with alcohol and taken up in 4 μl of loading buffer. The samples are then denatured at 95° C. for 3 min, removed by centrifugation and applied to a vertical polyacrylamide gel (34 cm in length, provided with 24 parallel lanes).

After excitation by an argon laser beam at 488 nm, the dyes emit light of different wavelengths of between 525 nm and 605 nm which is separated into its spectral colors via a grating, a "spectrograph". The spectral colors are subsequently detected simultaneously with the aid of the high-resolution pixel field of a CCD camera. The data are recorded with the aid of a computer (Macintosh Quadra/650 Macllcx Apple Share) and the corresponding data analysis software (PE Biosystems, Weiterstadt, Germany).

Sequencing gel: 30 g of urea (Sigma), 21.5 ml of distilled $H_2O$, 6 ml of 10×TBE The mixture is dissolved in a wide-necked flask on a heating block at 50° C., with the following being added: 9 ml of 40% bisacrylamide (filtered), 180 μl of 10% APS, 24 μl of Temed.

Polymerase Chain Reaction (PCR Reaction)

The following DNA polymerases may be used:

Taq (*Thermus aquaticus*) DNA polymerase (recombinant, Gibco/BRL) and 10×PCR buffer

[200 mM Tris/HCl (pH 8.4), 500 mM KCl]

Tfl (*Thermus flavus*) DNA polymerase (Master Amp™, Biozym, Oldendorf, Germany) and 20×PCR Buffer [20 mM $(NH_2)SO_4$, 1 M Tris/HCl (pH 9.0)

PCR Reaction Mixture:

| PCR components | Amount |
| --- | --- |
| DNA template | 10-100 ng |
| Starter molecule 1 | 25 μM |

-continued

| PCR components | Amount |
| --- | --- |
| Starter molecule 2 | 25 μM |
| Nucleotide mixture (dNTPs) | 20 mM (from a mixture containing 10 mM of each dNTP) |
| DNA polymerase buffer | 1x: 5.0 μl in the case of Taq DNA polymerase buffer |
| | 2.5 μl in the case of Tfl DNA polymerase buffer |
| $MgCl_2$ | 75 mM |
| DNA polymerase | 2 U in the case of Taq DNA polymerase |
| | 1 U in the case of Tfl DNA polymerase |
| Distilled $H_2O$ | to 50 μl total volume |

The following applies here: 1 U catalyses the conversion of 10 nM deoxyribonucleoside triphosphates, at 74° C. within 30 min, to an acid-insoluble DNA product. The PCR reaction usually commences with the "hot start": the mixture is incubated first without the polymerase at 94° C. in order to enable the DNA to be denatured for the first time. After the temperature has reached 80° C., the DNA polymerase is added to the mixture in order to avoid nonspecific amplification at a still low temperature. Thereafter, the actual PCR reaction is carried out over 25-35 cycles.

For each cycle, the following reaction conditions apply:

| Reaction | Temperature | Time |
| --- | --- | --- |
| Denaturation | 94° C. | 30-60 sec |
| Hybridization (annealing) | $T_m$-5° C. | 30-60 sec |
| Extension | 72° C. | 1 min/1 kb |

Finally and in addition, the chain extension is carried out at 72° C. for 10 min, finally followed by cooling.

Isolation of Total RNA

All centrifugation steps are carried out at 13 000 rpm and 16° C.

Cells are lysed with 600 μl of lysis buffer (100 RLT buffer: 1 mercaptoethanol). The cell lysate is applied to a QiaSchredder column and removed by centrifugation for 2 min.

The eluate is admixed with 600 μl of 70% ethanol, mixed well, and the DNA is applied to an RNAeasy mini spin column and centrifuged for 15 s (binding of RNA to the silica matrix). The column is washed three times (once with 700 ml of RW1 buffer and twice with 500 μl of RPE buffer). The column is then transferred to an autoclaved 1.5 ml Eppendorf tube and the RNA is eluated with 15 μl of distilled $H_2O$. The average concentration of total RNA obtained in this way is 1 μg/μl.

RNA Fractionation Via Agarose Gel Electrophoresis

Denaturing agarose gel:

1 g of agarose, 37 ml of distilled water, 10 ml of 10×MOPS (0.2 mM

MOPS, 10 mM EDTA, 100 mM NaAc), the mixture is boiled and cooled to 60° C.

16 ml of 37% strength formaldehyde are added.

After it has solidified, the gel is inserted with RNA gel running buffer into the electrophoresis apparatus. The RNA is applied together with a special sample buffer.

RNA gel running buffer: 40 ml of 10×MOPS, 65 ml of 37% strength formaldehyde, 295 ml of distilled water RNA sample buffer: 1-5 µg of RNA, 5 µl of RNA-NEW buffer (7.5 µl 37% strength formaldehyde, 4.5 µl of 10×MOPS, 25.9 µl of formamide, 7.5 µl of distilled water), 2 µl of formamide dye marker [50% (v/v) glycerol, 1 mM EDTA (pH 8.0), 0.25% (v/v) bromophenol blue, 0.25% (v/v) xylene cyanol].

The gel runs at 80 V for approx. 3 h. Since this work uses only eukaryotic RNA isolates, the dominant bands visible on the gel should be those of 28S and 18S rRNA.

Reverse Transcriptase with MMLV-RT (Moloney Murine Leukemia Virus—Reverse Transcriptase)

Reverse transcriptase mixture: 5 µg of RNA, 100 µM of starter molecule

The RNA preparation and the starter molecule are incubated at 75° C. for 10 min, in order to avoid possible formation of secondary structures in the RNA template as factors interfering with the transcriptase. However, even without this step, a transcription reaction usually takes place.

Reverse transcriptase reaction mixture: 28 U of Rnasin® (Promega), 25 mM dNTPS, 5 µl of 10× reverse transcriptase buffer [10 m Tris/HCl (pH 8.3), 75 mM KCl, 3 mM $MgCl_2$], 50 U of reverse transcriptase (StrataScript™, Stratagene), to 50 µl with distilled water.

The reverse transcription is carried out by incubating the mixture at 42° C. for 15 min and at 37° C. for 45 min. A longer incubation of 2 h at 42° C. with a 30-sec interruption at 55° C. is recommended for relatively long RNA templates. Subsequent incubation of the mixture at 95° C. for 5 minutes results in inactivation of said reverse transcriptase. Subsequently, 5-20 µl of the reverse transcription mixture are used for a PCR reaction.

Preparation of Genomic DNA from Tissue 100 mg of tissue are crushed in liquid nitrogen to give a powder. The tissue powder is introduced into a Falcon tube containing 6 ml of reaction buffer (30 µl of proteinase K [20 mg/ml] are added freshly to the buffer) and incubated with careful shaking at 56° C. overnight (12-18 hours). After incubation, 100 µl of RNase A (10 µg/µl) are added and the mixture is incubated with further shaking at 37° C. for one hour.

This is followed by adding 4 ml of phenol and turning the tube manually upside down and up again for approximately 5 min. 4 ml of Cl (chloroform/isoamyl alcohol) are added immediately and the tube is turned upside down and up again for another 5 minutes and then centrifuged for 15 min (3 000 rpm). The supernatant is carefully removed and transferred to 10 ml Falcon tubes. If the supernatant is still not clear, the phenol extraction must be repeated, otherwise another 4 ml of Cl are added and the tube is manually turned upside down and up for 5 min and then centrifuged for 15 min (3 000 rpm). The supernatant is carefully removed and the Cl extraction repeated. The final supernatant obtained is admixed with 1/10 volumes of sodium acetate solution (3 M, pH 6) and 2.5 volumes of ethanol (99.8%). The tube is carefully rotated, until the DNA precipitates as a tangle. This DNA tangle is transferred to approximately 25 ml of ethanol (70%) with the aid of a glass hook and left resting for 3 min. The washing was repeated twice. The DNA was then dried in air and dissolved in 0.5 ml of double-distilled water at room temperature.

Southern Blot

DNA Fractionation Via an Agarose Gel

Leave the gel on short-wave UV for approx. 5 min for strand breaks to occur in the larger DNA molecules (>6 kBp).

Continuously tilt the gel in denaturating solution for 30 min for DNA denaturation.

Continuously tilt the gel in neutralizing solution for 30 min for neutralization.

Blot construction (from bottom to top): gel, nylon membrane, dry filter paper, blotting paper, plate, weight (approx. 1 kg).

Blotting with 20×SCC overnight.

Wash membrane in 2×SSC for 10 min

Dry membrane on filter paper

Fixing of nucleic acid by baking at 80° C. for 1 h or UV crosslinking (e.g. in "Stratalinker", automatic position). The membrane may then be stored until hybridization.

Prehybridization of membrane in hybridization solution for approx. 1-2 h Covering of nonspecific binding sites on the membrane.

Hybridization solution: 5×SSC, 5×Denhardt's solution, 0.5% SDS, 100 µg/ml herring sperm DNA Denaturing solution: 0.5 M NaOH (20 g), 1 M NaCl Neutralizing solution: 1.5 M NaCl/0.5 M Tris pH 7.4

20×SSC is 3 M NaCl, 0.3 M Na-citrate: 175.3 g of NaCl, 88.2 g of sodium citrate X 2 $H_2O$, to 1 l with double-distilled water, adjust pH to 7.0 with HCl.

50×Denhard's solution: 5 g of Ficoll 400, 5 g of PVP (polyvinyl pyrrolidone), 5 g of BSA, to 500 ml with double-distilled water Northern Blot RNA Fractionation Using a Formaldehyde Agarose Gel Blot construction (from bottom to top): gel, nylon membrane, dry filter paper, blotting paper, plate, weight (appox. 1 kg).

Blotting with 20×SSC overnight.

Fix RNA on filter by baking at 80° C. (1 h)

Introduce filter into boiling 20 mM Tris pH 8 for RNA deglyoxylation and let cool to RT.

What is claimed is:

1. An isolated polynucleotide consisting of nucleotide 3090 to nucleotide 3329 of SEQ ID NO: 4.

2. A method of determining a patient's relative risk of a cardiovascular disorder, comprising:
   a. obtaining a nucleic acid sample from the patient; and
   b. determining the presence in the nucleic acid sample of at least one single nucleotide polymorphism of the PAR1 gene, selected from the group of polymorphisms corresponding to a C for T substitution at position 3090 and a C for A substitution at position 3329 of SEQ ID NO: 1;
   wherein the presence of the at least one polymorphism is diagnostic of a patient's relative risk of atrial fibrillation, acute coronary syndrome, cardiomyopathy or unstable angina.

3. The method of claim 2, wherein the step of determining the presence of at least one single nucleotide polymorphism comprises amplification of a portion of the nucleic acid sample comprising position 3090 of SEQ ID NO: 1 by polymerase chain reaction.

4. The method of claim 2, wherein the step of determining the presence of at least one single nucleotide polymorphism comprises amplification of a portion of the nucleic acid sample comprising position 3329 of SEQ ID NO: 1 by polymerase chain reaction.

5. The method of claim 2, wherein the step of determining the presence of at least one single nucleotide polymorphism comprises sequencing of a portion of the nucleic acid sample comprising position 3090 of SEQ ID NO: 1.

6. The method of claim 2, wherein the step of determining the presence of at least one single nucleotide polymorphism comprises sequencing of a portion of the nucleic acid sample comprising position 3329 of SEQ ID NO: 1.

* * * * *

SEQUENCE LISTING

```
<160> NUMBER OF SEQ ID NOS: 13

<210> SEQ ID NO 1
<211> LENGTH: 3592
<212> TYPE: DNA
<213> ORGANISM: Homo sapiens

<400> SEQUENCE: 1 ggcgggggggc gcacagagcc agaggggctt gcgagcggcg gctgagggac cgcggggagg      60
```

```
gggcgccgag cggctccagc gcagagactc tcactgcacg ccggaggccc cttcctcgct      120
ccgcccgcgc gaccgcgcgc cccagtcccg ccccgccccg ctaaccgccc cagacacagc      180
gctcgccgag ggtcgcttgg accctgatct tacccgtggg caccctgcgc tctgcctgcc      240
gcgaagaccg gctccccgac ccgcagaagt caggagagag ggtgaagcgg agcagcccga      300
ggcggggcag cctcccggag cagcgccgcg cagagcccgg gacaatgggg ccgcggcggc      360
tgctgctggt ggccgcctgc ttcagtctgt gcggcccgct gttgtctgcc cgcacccggg      420
cccgcaggcc agaatcaaaa gcaacaaatg ccaccttaga tccccggtca tttcttctca      480
ggaaccccaa tgataaatat gaaccatttt gggaggatga ggagaaaaat gaaagtgggt      540
taactgaata cagattagtc tccatcaata aaagcagtcc tcttcaaaaa caacttcctg      600
cattcatctc agaagatgcc tccggatatt tgaccagctc ctggctgaca ctctttgtcc      660
catctgtgta caccggagtg tttgtagtca gcctcccact aaacatcatg gccatcgttg      720
tgttcatcct gaaaatgaag gtcaagaagc cggcggtggt gtacatgctg cacctggcca      780
cggcagatgt gctgtttgtg tctgtgctcc cctttaagat cagctattac ttttccggca      840
gtgattggca gtttgggtct gaattgtgtc gcttcgtcac tgcagcattt tactgtaaca      900
tgtacgcctc tatcttgctc atgacagtca taagcattga ccggtttctg gctgtggtgt      960
atcccatgca gtccctctcc tggcgtactc tgggaagggc ttccttcact tgtctggcca     1020
tctgggcttt ggccatcgca ggggtagtgc ctctcgtcct caaggagcaa accatccagg     1080
tgcccgggct caacatcact acctgtcatg atgtgctcaa tgaaccctg ctcgaaggct      1140 actatgccta ctacttctca gccttctctg ctgtcttctt ttttgtgccg ctgatcattt     1200
ccacggtctg ttatgtgtct atcattgat gtcttagctc ttccgcagtt gccaaccgca     1260
gcaagaagtc ccgggctttg ttcctgtcag ctgctgtttt ctgcatcttc atcatttgct     1320
tcggacccac aaaacgtcctc ctgattgcgc attactcatt cctttctcac acttccacca     1380
cagaggctgc ctactttgcc tacctcctct gtgtctgtgt cagcagcata agctcgtgca     1440
tcgaccccct aatttactat tacgcttcct ctgagtgcca gaggtacgtc tacagtatct     1500
tatgctgcaa agaaagttcc gatcccagca gttataacag cagtgggcag ttgatggcaa     1560
gtaaaatgga tacctgctct agtaacctga ataacagcat atacaaaaag ctgttaactt     1620
aggaaaaggg actgctggga ggttaaaaag aaaagtttat aaaagtgaat aacctgagga     1680
ttctattagt ccccacccaa actttattga ttcacctcct aaaacaacag atgtacgact     1740
tgcatacctg cttttttatgg gagctgtcaa gcatgtattt ttgtcaatta ccagaaagat     1800
aacaggacga gatgacggtg ttattccaag ggaatattgc caatgctaca gtaataaatg     1860
aatgtcactt ctggatatag ctaggtgaca tatacatact tacatgtgtg tatatgtaga     1920
tgtatgcaca cacatatatt atttgcagtg cagtatagaa taggcacttt aaaacactct     1980
ttccccgcac cccagcaatt atgaaaataa tctctgattc cctgatttaa tatgcaaagt     2040
ctaggttggt agagtttagc cctgaacatt tcatggtgtt catcaacagt gagagactcc     2100
atagtttggg cttgtaccac ttttgcaaat aagtgtattt tgaaattgtt tgacggcaag     2160
gtttaagtta ttaagaggta agacttagta ctatctgtgc gtagaagttc tagtgttttc     2220
aattttaaac atatccaagt ttgaattcct aaaattatgg aaacagatga aaagcctctg     2280
ttttgatatg ggtagtattt tttacatttt acacactgta cacataagcc aaaactgagc     2340
ataagtcctc tagtgaatgt aggctggctt tcagagtagg ctattcctga gagctgcatg     2400
```

| | | | | |
|---|---|---|---|---|
| tgtccgcccc | cgatggagga | ctccaggcag | cagacacatg | ccagggccat gtcagacaca | 2460 |
| gattggccag | aaaccttcct | gctgagcctc | acagcagtga | gactgggcc actacatttg | 2520 |
| ctccatcctc | ctgggattgg | ctgtgaactg | atcatgttta | tgagaaactg gcaaagcaga | 2580 |
| atgtgatatc | ctaggaggta | atgaccatga | aagacttctc | tacccatctt aaaaacaacg | 2640 |
| aaagaaggca | tggacttctg | gatgcccatc | cactgggtgt | aaacacatct agtagttgtt | 2700 |
| ctgaaatgtc | agttctgata | tggaagcacc | cattatgcgc | tgtggccact ccaataggtg | 2760 |
| ctgagtgtac | agagtggaat | aagacagaga | cctgccctca | agagcaaagt agatcatgca | 2820 |
| tagagtgtga | tgtatgtgta | ataaatatgt | ttcacacaaa | caaggcctgt cagctaaaga | 2880 |
| agtttgaaca | tttgggttac | tatttcttgt | ggttataact | taatgaaaac aatgcagtac | 2940 |
| aggacatata | ttttttaaaa | taagtctgat | ttaattgggc | actatttatt tacaaatgtt | 3000 |
| ttgctcaata | gattgctcaa | atcaggtttt | cttttaagaa | tcaatcatgt cagtctgctt | 3060 |
| agaaataaca | gaagaaaata | gaattgacat | tgaaatctag | gaaaattatt ctataatttc | 3120 |
| catttactta | agacttaatg | agactttaaa | agcattttt | aacctcctaa gtatcaagta | 3180 |
| tagaaaatct | tcatggaatt | cacaaagtaa | tttggaaatt | aggttgaaac atatctctta | 3240 |
| tcttacgaaa | aaatggtagc | attttaaaca | aaatagaaag | ttgcaaggca aatgtttatt | 3300 |
| taaaagagca | ggccaggcgc | ggtggctcac | gcctgtaatc | ccagcacttt gggaggctga | 3360 |
| ggcgggtgga | tcacgaggtc | aggagatcga | gaccatcctg | gctaacacgg tgaaacccgt | 3420 |
| ctctactaaa | aatgcaaaaa | aaattagccg | ggcgtggtgg | caggcacctg tagtcccagc | 3480 |
| tactcgggag | gctgaggcag | gagactggcg | tgaacccagg | aggcggacct tgtagtgagc | 3540 |
| cgagatcgcg | ccactgtgct | ccagcctggg | caacagagca | agactccatc tc | 3592 |

<210> SEQ ID NO 2
<211> LENGTH: 3592
<212> TYPE: DNA
<213> ORGANISM: Homo sapiens

<400> SEQUENCE: 2

| | | | | |
|---|---|---|---|---|
| ggcggggggc | gcacagagcc | agagggctt | gcgagcggcg | gctgagggac cgcggggagg | 60 |
| gggcgccgag | cggctccagc | gcagagactc | tcactgcacg | ccggaggccc cttcctcgct | 120 |
| ccgcccgcgc | gaccgcgcgc | cccagtcccg | ccccgccccg | ctaaccgccc cagacacagc | 180 |
| gctcgccgag | ggtcgcttgg | accctgatct | tacccgtggg | caccctgcgc tctgcctgcc | 240 |
| gcgaagaccg | gctccccgac | ccgcagaagt | caggagagag | ggtgaagcgg agcagcccga | 300 |
| ggcggggcag | cctcccggag | cagcgccgcg | cagagcccgg | gacaatgggg ccgcggcggc | 360 |
| tgctgctggt | ggccgcctgc | ttcagtctgt | gcggcccgct | gttgtctgcc cgcacccggg | 420 |
| cccgcaggcc | agaatcaaaa | gcaacaaatg | ccaccttaga | tccccggtca tttcttctca | 480 |
| ggaaccccaa | tgataaatat | gaaccatttt | gggaggatga | ggagaaaaat gaaagtgggg | 540 |
| taactgaata | cagattagtc | tccatcaata | aaagcagtcc | tcttcaaaaa caacttcctg | 600 |
| cattcatctc | agaagatgcc | tccggatatt | tgaccagctc | ctggctgaca ctcttgtcc | 660 |
| catctgtgta | caccggagtg | tttgtagtca | gcctcccact | aaacatcatg gccatcgttg | 720 |
| tgttcatcct | gaaaatgaag | gtcaagaagc | cggcggtggt | gtacatgctg cacctggcca | 780 |
| cggcagatgt | gctgtttgtg | tctgtgctcc | cctttaagat | cagctattac ttttccggca | 840 |
| gtgattggca | gtttgggtct | gaattgtgtc | gcttcgtcac | tgcagcattt tactgtaaca | 900 |
| tgtacgcctc | tatcttgctc | atgacagtca | taagcattga | ccggtttctg gctgtggtgt | 960 |

-continued

```
atcccatgca gtccctctcc tggcgtactc tgggaagggc ttccttcact tgtctggcca    1020
tctgggcttt ggccatcgca ggggtagtgc ctctcgtcct caaggagcaa accatccagg    1080
tgcccgggct caacatcact acctgtcatg atgtgctcaa tgaaaccctg ctcgaaggct    1140
actatgccta ctacttctca gccttctctg ctgtcttctt ttttgtgccg ctgatcattt    1200
ccacggtctg ttatgtgtct atcattcgat gtcttagctc ttccgcagtt gccaaccgca    1260
gcaagaagtc ccgggctttg ttcctgtcag ctgctgtttt ctgcatcttc atcatttgct    1320
tcggacccac aaacgtcctc ctgattgcgc attactcatt cctttctcac acttccacca    1380
cagaggctgc ctactttgcc tacctcctct gtgtctgtgt cagcagcata agctcgtgca    1440
tcgaccccct aatttactat tacgcttcct ctgagtgcca gaggtacgtc tacagtatct    1500
tatgctgcaa agaaagttcc gatcccagca gttataacag cagtgggcag ttgatggcaa    1560
gtaaaatgga tacctgctct agtaacctga ataacagcat atacaaaaag ctgttaactt    1620
aggaaaaggg actgctggga ggttaaaaag aaaagtttat aaaagtgaat aacctgagga    1680
ttctattagt ccccacccaa actttattga ttcacctcct aaaacaacag atgtacgact    1740
tgcatacctg cttttttatgg gagctgtcaa gcatgtattt ttgtcaatta ccagaaagat    1800
aacaggacga gatgacggtg ttattccaag ggaatattgc caatgctaca gtaataaatg    1860
aatgtcactt ctggatatag ctaggtgaca tatacatact tacatgtgtg tatatgtaga    1920
tgtatgcaca cacatatatt atttgcagtg cagtatagaa taggcacttt aaaacactct    1980
ttccccgcac cccagcaatt atgaaaataa tctctgattc cctgatttaa tatgcaaagt    2040
ctaggttggt agagtttagc cctgaacatt tcatggtgtt catcaacagt gagagactcc    2100
atagtttggg cttgtaccac ttttgcaaat aagtgtattt tgaaattgtt tgacggcaag    2160
gtttaagtta ttaagaggta agacttagta ctatctgtgc gtagaagttc tagtgttttc    2220
aattttaaac atatccaagt ttgaattcct aaaattatgg aaacagatga aaagcctctg    2280
ttttgatatg ggtagtattt tttacatttt acacactgta cacataagcc aaaactgagc    2340
ataagtcctc tagtgaatgt aggctggctt tcagagtagg ctattcctga gagctgcatg    2400
tgtccgcccc cgatggagga ctccaggcag cagacacatg ccagggccat gtcagacaca    2460
gattggccag aaaccttcct gctgagcct acagcagtga gactgggcc actacatttg    2520 ctccatcctc ctgggattgg ctgtgaactg atcatgttta tgagaaactg gcaaagcaga    2580
atgtgatatc ctaggaggta atgaccatga aagacttctc tacccatctt aaaaacaacg    2640
aaagaaggca tggacttctg gatgcccatc cactgggtgt aaacacatct agtagttgtt    2700
ctgaaatgtc agttctgata tggaagcacc cattatgcgc tgtggccact ccaataggtg    2760
ctgagtgtac agagtggaat aagacagaga cctgccctca gagcaaagt agatcatgca    2820 tagagtgtga tgtatgtgta ataaatatgt ttcacacaaa caaggcctgt cagctaaaga    2880
agtttgaaca tttgggttac tatttcttgt ggttataact taatgaaaac aatgcagtac    2940
aggacatata ttttttaaaa taagtctgat ttaattgggc actatttatt tacaaatgtt    3000
ttgctcaata gattgctcaa atcaggtttt cttttaagaa tcaatcatgt cagtctgctt    3060
agaaataaca aagaaaata gaattgacac tgaaatctag gaaaattatt ctataatttc    3120
catttactta agacttaatg agactttaaa agcatttttt aacctcctaa gtatcaagta    3180
tagaaaatct tcatggaatt cacaaagtaa tttggaaatt aggttgaaac atatctctta    3240
tcttacgaaa aaatggtagc attttaaaca aaatagaaag ttgcaaggca aatgtttatt    3300
```

-continued

```
taaaagagca ggccaggcgc ggtggctcac gcctgtaatc ccagcacttt gggaggctga      3360
ggcgggtgga tcacgaggtc aggagatcga accatcctg gctaacacgg tgaaacccgt       3420
ctctactaaa aatgcaaaaa aaattagccg ggcgtggtgg caggcacctg tagtcccagc      3480
tactcgggag gctgaggcag gagactggcg tgaacccagg aggcggacct tgtagtgagc      3540
cgagatcgcg ccactgtgct ccagcctggg caacagagca agactccatc tc              3592

<210> SEQ ID NO 3
<211> LENGTH: 3592
<212> TYPE: DNA
<213> ORGANISM: Homo sapiens

<400> SEQUENCE: 3
ggcggggggc gcacagagcc agaggggctt gcgagcggcg gctgagggac cgcggggagg        60
gggcgccgag cggctccagc gcagagactc tcactgcacg ccggaggccc cttcctcgct       120
ccgcccgcgc gaccgcgcgc cccagtcccg ccccgccccg ctaaccgccc cagacacagc       180
gctcgccgag ggtcgcttgg accctgatct tacccgtggg caccctgcgc tctgcctgcc      240
gcgaagaccg gctccccgac ccgcagaagt caggagagag ggtgaagcgg agcagcccga       300
ggcggggcag cctcccggag cagcgccgcg cagagcccgg acaatggggg ccgcggcggc       360
tgctgctggt ggccgcctgc ttcagtctgt gcggcccgct gttgtctgcc cgcacccggg       420
cccgcaggcc agaatcaaaa gcaacaaatg ccaccttaga tccccggtca tttcttctca      480
ggaaccccaa tgataaatat gaaccatttt ggggaggatga ggagaaaaat gaaagtgggt      540
taactgaata cagattagtc tccatcaata aaagcagtcc tcttcaaaaa caacttcctg       600
cattcatctc agaagatgcc tccggatatt tgaccagctc ctggctgaca ctctttgtcc      660
catctgtgta caccggagtg tttgtagtca gcctcccact aaacatcatg gccatcgttg      720
tgttcatcct gaaaatgaag gtcaagaagc cggcggtggt gtacatgctg cacctggcca      780
cggcagatgt gctgtttgtg tctgtgctcc ccttttaagat cagctattac ttttccggca      840
gtgattggca gtttgggtct gaattgtgtc gcttcgtcac tgcagcattt tactgtaaca      900
tgtacgcctc tatcttgctc atgacagtca taagcattga ccggtttctg gctgtggtgt      960 atccccatgca gtccctctcc tggcgtactc tgggaagggc ttccttcact tgtctggcca     1020
tctgggcttt ggccatcgca ggggtagtgc ctctcgtcct caaggagcaa accatccagg      1080
tgcccgggct caacatcact acctgtcatg atgtgctcaa tgaaaccctg ctcgaaggct      1140
actatgccta ctacttctca gccttctctg ctgtcttctt ttttgtgccg ctgatcattt      1200
ccacggtctg ttatgtgtct atcattcgat gtcttagctc ttccgcagtt gccaaccgca     1260
gcaagaagtc ccgggctttg ttcctgtcag ctgctgtttt ctgcatcttc atcatttgct     1320
tcggacccac aaacgtcctc ctgattgcgc attactcatt cctttctcac acttccacca     1380
cagaggctgc ctactttgcc tacctcctct gtgtctgtgt cagcagcata agctcgtgca     1440 tcgacccct aatttactat tacgcttcct ctgagtgcca gaggtacgtc tacagtatct      1500
tatgctgcaa agaagttcc gatcccagca gttataacag cagtgggcag ttgatggcaa      1560
gtaaaatgga tacctgctct agtaacctga ataacagcat atacaaaaag ctgttaactt      1620
aggaaaaggg actgctggga ggttaaaaag aaaagtttat aaaagtgaat aacctgagga      1680
ttctattagt ccccacccaa actttattga ttcacctcct aaaacaacag atgtacgact      1740
tgcatacctg cttttttatgg gagctgtcaa gcatgtatt ttgtcaatta ccagaaagat      1800
aacaggacga gatgacggtg ttattccaag ggaatattgc caatgctaca gtaataaatg      1860
```

```
aatgtcactt ctggatatag ctaggtgaca tatacatact tacatgtgtg tatatgtaga    1920
tgtatgcaca cacatatatt atttgcagtg cagtatagaa taggcacttt aaaacactct    1980
ttccccgcac cccagcaatt atgaaaataa tctctgattc cctgatttaa tatgcaaagt    2040
ctaggttggt agagtttagc cctgaacatt tcatggtgtt catcaacagt gagagactcc    2100
atagtttggg cttgtaccac ttttgcaaat aagtgtattt tgaaattgtt tgacggcaag    2160
gtttaagtta ttaagaggta agacttagta ctatctgtgc gtagaagttc tagtgttttc    2220
aattttaaac atatccaagt ttgaattcct aaaattatgg aaacagatga aaagcctctg    2280
ttttgatatg ggtagtattt tttacatttt acacactgta cacataagcc aaaactgagc    2340
ataagtcctc tagtgaatgt aggctggctt tcagagtagg ctattcctga gagctgcatg    2400
tgtccgcccc cgatggagga ctccaggcag cagacacatg ccagggccat gtcagacaca    2460
gattggccag aaaccttcct gctgagcctc acagcagtga gactgggcc actacatttg     2520 ctccatcctc ctgggattgg ctgtgaactg atcatgttta tgagaaactg gcaaagcaga    2580
atgtgatatc ctaggaggta atgaccatga aagacttctc tacccatctt aaaaacaacg    2640
aaagaaggca tggacttctg gatgcccatc cactgggtgt aaacacatct agtagttgtt    2700
ctgaaatgtc agttctgata tggaagcacc cattatgcgc tgtggccact ccaataggtg    2760
ctgagtgtac agagtggaat aagacagaga cctgccctca agagcaaagt agatcatgca    2820
tagagtgtga tgtatgtgta ataaatatgt tcacacaaa caaggcctgt cagctaaaga     2880
agtttgaaca tttgggttac tatttcttgt ggttataact taatgaaaac aatgcagtac    2940
aggacatata tttttaaaa taagtctgat ttaattgggc actatttatt tacaaatgtt     3000
ttgctcaata gattgctcaa atcaggtttt cttttaagaa tcaatcatgt cagtctgctt    3060
agaaataaca gaagaaaata gaattgacat tgaaatctag gaaaattatt ctataatttc    3120
catttactta agacttaatg agactttaaa agcatttttt aacctcctaa gtatcaagta    3180
tagaaaatct tcatggaatt cacaaagtaa tttggaaatt aggttgaaac atatctctta    3240
tcttacgaaa aaatggtagc attttaaaca aaatagaaag ttgcaaggca aatgtttatt    3300
taaaagagca ggccaggcgc ggtggctccc gcctgtaatc ccagcacttt gggaggctga    3360
ggcgggtgga tcacgaggtc aggagatcga accatcctg gctaacacgg tgaaaccccgt     3420 ctctactaaa aatgcaaaaa aaattagccg ggcgtggtgg caggcacctg tagtcccagc    3480
tactcgggag gctgaggcag gagactggcg tgaacccagg aggcggacct tgtagtgagc    3540
cgagatcgcg ccactgtgct ccagcctggg caacagagca agactccatc tc            3592
```

<210> SEQ ID NO 4
<211> LENGTH: 3592
<212> TYPE: DNA
<213> ORGANISM: Homo sapiens

<400> SEQUENCE: 4

```
ggcggggggc gcacagagcc agaggggctt gcgagcggcg gctgagggac cgcggggagg      60
gggcgccgag cggctccagc gcagagactc tcactgcacg ccggaggccc cttcctcgct     120
ccgcccgcgc gaccgcgcgc cccagtcccg ccccgcccg ctaaccgccc cagacacagc      180
gctcgccgag ggtcgcttgg accctgatct tacccgtggg caccctgcgc tctgcctgcc     240
gcgaagaccg gctccccgac ccgcagaagt caggagagag ggtgaagcgg agcagcccga     300
ggcggggcag cctcccggag cagcgccgcg cagagcccgg gacaatgggg ccgcggcggc     360
```

-continued

```
tgctgctggt ggccgcctgc ttcagtctgt gcggcccgct gttgtctgcc cgcacccggg    420
cccgcaggcc agaatcaaaa gcaacaaatg ccaccttaga tccccggtca tttcttctca    480
ggaaccccaa tgataaatat gaaccatttt gggaggatga ggagaaaaat gaaagtgggt    540
taactgaata cagattagtc tccatcaata aaagcagtcc tcttcaaaaa caacttcctg    600
cattcatctc agaagatgcc tccggatatt tgaccagctc ctggctgaca ctctttgtcc    660
catctgtgta caccggagtg tttgtagtca gcctcccact aaacatcatg gccatcgttg    720
tgttcatcct gaaaatgaag gtcaagaagc cggcggtggt gtacatgctg cacctggcca    780
cggcagatgt gctgtttgtg tctgtgctcc cctttaagat cagctattac ttttccggca    840
gtgattggca gtttgggtct gaattgtgtc gcttcgtcac tgcagcattt tactgtaaca    900
tgtacgcctc tatcttgctc atgacagtca taagcattga ccggtttctg ctgtggtgt    960 atcccatgca gtccctctcc tggcgtactc tgggaagggc ttccttcact tgtctggcca   1020
tctgggcttt ggccatcgca ggggtagtgc ctctcgtcct caaggagcaa accatccagg   1080
tgcccgggct caacatcact acctgtcatg atgtgctcaa tgaaaccctg ctcgaaggct   1140
actatgccta ctacttctca gccttctctg ctgtcttctt ttttgtgccg ctgatcattt   1200
ccacggtctg ttatgtgtct atcattcgat gtcttagctc ttccgcagtt gccaaccgca   1260
gcaagaagtc ccgggctttg ttcctgtcag ctgctgtttt ctgcatcttc atcatttgct   1320
tcggacccac aaacgtcctc ctgattgcgc attactcatt cctttctcac acttccacca   1380
cagaggctgc ctactttgcc tacctcctct gtgtctgtgt cagcagcata agctcgtgca   1440 tcgacccct aatttactat tacgcttcct ctgagtgcca gaggtacgtc tacagtatct   1500
tatgctgcaa agaaagttcc gatcccagca gttataacag cagtgggcag ttgatggcaa   1560
gtaaaatgga tacctgctct agtaacctga ataacagcat atacaaaaag ctgttaactt   1620
aggaaaaggg actgctggga ggttaaaaag aaaagtttat aaaagtgaat aacctgagga   1680
ttctattagt ccccacccaa actttattga ttcacctcct aaaacaacag atgtacgact   1740
tgcatacctg ctttttatgg gagctgtcaa gcatgtattt ttgtcaatta ccagaaagat   1800
aacaggacga gatgacggtg ttattccaag ggaatattgc caatgctaca gtaataaatg   1860
aatgtcactt ctggatatag ctaggtgaca tatacatact tacatgtgtg tatatgtaga   1920
tgtatgcaca cacatatatt atttgcagtg cagtatagaa taggcacttt aaaacactct   1980
ttccccgcac cccagcaatt atgaaaataa tctctgattc cctgatttaa tatgcaaagt   2040
ctaggttggt agagtttagc cctgaacatt tcatggtgtt catcaacagt gagagactcc   2100
atagtttggg cttgtaccac ttttgcaaat aagtgtattt tgaaattgtt tgacggcaag   2160
gtttaagtta ttaagaggta agacttagta ctatctgtgc gtagaagttc tagtgttttc   2220
aattttaaac atatccaagt ttgaattcct aaaattatgg aaacagatga aaagcctctg   2280
ttttgatatg ggtagtattt tttacatttt acacactgta cacataagcc aaaactgagc   2340
ataagtcctc tagtgaatgt aggctggctt tcagagtagg ctattcctga gagctgcatg   2400
tgtccgcccc cgatggagga ctccaggcag cagacacatg ccagggccat gtcagacaca   2460
gattggccag aaaccttcct gctgagcctc acagcagtga gactggggcc actacatttg   2520
ctccatcctc ctgggattgg ctgtgaactg atcatgttta tgagaaactg gcaaagcaga   2580
atgtgatatc ctaggaggta atgaccatga aagacttctc tacccatctt aaaaacaacg   2640
aaagaaggca tggacttctg gatgcccatc cactgggtgt aaacacatct agtagttgtt   2700
ctgaaatgtc agttctgata tggaagcacc cattatgcgc tgtggccact ccaataggtg   2760
```

-continued

```
ctgagtgtac agagtggaat aagacagaga cctgccctca agagcaaagt agatcatgca   2820
tagagtgtga tgtatgtgta ataaatatgt tcacacaaa caaggcctgt cagctaaaga    2880
agtttgaaca tttgggttac tatttcttgt ggttataact taatgaaaac aatgcagtac   2940
aggacatata ttttttaaaa taagtctgat ttaattgggc actatttatt tacaaatgtt   3000
ttgctcaata gattgctcaa atcaggtttt cttttaagaa tcaatcatgt cagtctgctt   3060
agaaataaca gaagaaaata gaattgacac tgaaatctag gaaaattatt ctataatttc   3120
catttactta agacttaatg agactttaaa agcattttt aacctcctaa gtatcaagta    3180
tagaaaatct tcatggaatt cacaaagtaa tttggaaatt aggttgaaac atatctctta   3240
tcttacgaaa aaatggtagc attttaaaca aaatagaaag ttgcaaggca aatgtttatt   3300
taaaagagca ggccaggcgc ggtggctccc gcctgtaatc ccagcacttt gggaggctga   3360
ggcgggtgga tcacgaggtc aggagatcga gaccatcctg gctaacacgg tgaaacccgt   3420
ctctactaaa aatgcaaaaa aaattagccg ggcgtggtgg caggcacctg tagtcccagc   3480
tactcgggag gctgaggcag gagactggcg tgaacccagg aggcggacct tgtagtgagc   3540
cgagatcgcg ccactgtgct ccagcctggg caacagagca agactccatc tc           3592

<210> SEQ ID NO 5
<211> LENGTH: 939
<212> TYPE: DNA
<213> ORGANISM: Homo sapiens

<400> SEQUENCE: 5
acagagtgga ataagacaga gacctgccct caagagcaaa gtagatcatg catagagtgt    60
gatgtatgtg taataaatat gtttcacaca aacaaggcct gtcagctaaa gaagtttgaa   120
catttgggtt actatttctt gtggttataa cttaatgaaa acaatgcagt acaggacata   180
tattttttaa aataagtctg atttaattgg gcactattta tttacaaatg ttttgctcaa   240
tagattgctc aaatcaggtt ttcttttaag aatcaatcat gtcagtctgc ttagaaataa   300
cagaagaaaa tagaattgac attgaaatct aggaaaatta ttctataatt tccatttact   360
taagacttaa tgagactttta aaagcatttt ttaacctcct aagtatcaag tatagaaaat   420
cttcatggaa ttcacaaagt aatttggaaa ttaggttgaa acatatctct tatcttacga   480
aaaaatggta gcattttaaa caaaatagaa agttgcaagg caaatgttta tttaaaagag   540
caggccaggc gcggtggctc acgcctgtaa tcccagcact ttgggaggct gaggcgggtg   600
gatcacgagg tcaggagatc gagaccatcc tggctaacac ggtgaaaccc gtctctacta   660
aaaatgcaaa aaaattagcc gggcgtggtg gcaggcacc tgtagtccca gctactcggg    720
aggctgaggc aggagactgg cgtgaaccca ggaggcggac cttgtagtga gccgagatcg   780
cgccactgtg ctccagcctg gcaacagag caagactcca tctcaaaaaa taaaaataaa    840 taaaaataa aaaataaaa gagcaaacta tttccaaata ccatagaata acttacataa    900
aagtaatata actgtattgt aagtagaagc tagcactgg                         939

<210> SEQ ID NO 6
<211> LENGTH: 939
<212> TYPE: DNA
<213> ORGANISM: Homo sapiens

<400> SEQUENCE: 6
acagagtgga ataagacaga gacctgccct caagagcaaa gtagatcatg catagagtgt    60
```

```
gatgtatgtg taataaatat gtttcacaca aacaaggcct gtcagctaaa gaagtttgaa      120
catttgggtt actatttctt gtggttataa cttaatgaaa acaatgcagt acaggacata      180
tattttttaa aataagtctg atttaattgg gcactattta tttacaaatg ttttgctcaa      240
tagattgctc aaatcaggtt ttcttttaag aatcaatcat gtcagtctgc ttagaaataa      300
cagaagaaaa tagaattgac actgaaatct aggaaaatta ttctataatt tccatttact      360
taagacttaa tgagacttta aaagcatttt ttaacctcct aagtatcaag tatagaaaat      420
cttcatggaa ttcacaaagt aatttggaaa ttaggttgaa acatatctct tatcttacga      480
aaaaatggta gcattttaaa caaaatagaa agttgcaagg caaatgttta tttaaaagag      540
caggccaggc gcggtggctc acgcctgtaa tcccagcact tgggaggct gaggcgggtg       600 gatcacgagg tcaggagatc gagaccatcc tggctaacac ggtgaaaccc gtctctacta      660
aaaatgcaaa aaaaattagc cgggcgtggt ggcaggcacc tgtagtccca gctactcggg      720
aggctgaggc aggagactgg cgtgaaccca ggaggcggac cttgtagtga ccgagatcg       780 cgccactgtg ctccagcctg gcaacagag caagactcca tctcaaaaaa taaaaataaa       840
taaaaaataa aaaataaaa gagcaaacta tttccaaata ccatagaata acttacataa       900
aagtaatata actgtattgt aagtagaagc tagcactgg                             939
```

```
<210> SEQ ID NO 7
<211> LENGTH: 939
<212> TYPE: DNA
<213> ORGANISM: Homo sapiens

<400> SEQUENCE: 7
```

```
acagagtgga ataagacaga gacctgccct caagagcaaa gtagatcatg catagagtgt       60
gatgtatgtg taataaatat gtttcacaca aacaaggcct gtcagctaaa gaagtttgaa      120
catttgggtt actatttctt gtggttataa cttaatgaaa acaatgcagt acaggacata      180
tattttttaa aataagtctg atttaattgg gcactattta tttacaaatg ttttgctcaa      240
tagattgctc aaatcaggtt ttcttttaag aatcaatcat gtcagtctgc ttagaaataa      300
cagaagaaaa tagaattgac attgaaatct aggaaaatta ttctataatt tccatttact      360
taagacttaa tgagacttta aaagcatttt ttaacctcct aagtatcaag tatagaaaat      420
cttcatggaa ttcacaaagt aatttggaaa ttaggttgaa acatatctct tatcttacga      480
aaaaatggta gcattttaaa caaaatagaa agttgcaagg caaatgttta tttaaaagag      540
caggccaggc gcggtggctc ccgcctgtaa tcccagcact tgggaggct gaggcgggtg       600 gatcacgagg tcaggagatc gagaccatcc tggctaacac ggtgaaaccc gtctctacta      660
aaaatgcaaa aaaaattagc cgggcgtggt ggcaggcacc tgtagtccca gctactcggg      720
aggctgaggc aggagactgg cgtgaaccca ggaggcggac cttgtagtga ccgagatcg       780 cgccactgtg ctccagcctg gcaacagag caagactcca tctcaaaaaa taaaaataaa       840
taaaaaataa aaaataaaa gagcaaacta tttccaaata ccatagaata acttacataa       900
aagtaatata actgtattgt aagtagaagc tagcactgg                             939
```

```
<210> SEQ ID NO 8
<211> LENGTH: 939
<212> TYPE: DNA
<213> ORGANISM: Homo sapiens

<400> SEQUENCE: 8
```

```
acagagtgga ataagacaga gacctgccct caagagcaaa gtagatcatg catagagtgt       60
```

-continued

```
gatgtatgtg taataaatat gtttcacaca aacaaggcct gtcagctaaa gaagtttgaa    120
catttgggtt actatttctt gtggttataa cttaatgaaa acaatgcagt acaggacata    180
tattttttaa aataagtctg atttaattgg gcactattta tttacaaatg ttttgctcaa    240
tagattgctc aaatcaggtt ttcttttaag aatcaatcat gtcagtctgc ttagaaataa    300
cagaagaaaa tagaattgac actgaaatct aggaaaatta ttctataatt tccatttact    360
taagacttaa tgagacttta aaagcatttt ttaacctcct aagtatcaag tatagaaaat    420
cttcatggaa ttcacaaagt aatttggaaa ttaggttgaa acatatctct tatcttacga    480
aaaaatggta gcattttaaa caaaatagaa agttgcaagg caaatgttta tttaaaagag    540
caggccaggc gcggtggctc ccgcctgtaa tcccagcact tgggaggct gaggcgggtg     600 gatcacgagg tcaggagatc gagaccatcc tggctaacac ggtgaaaccc gtctctacta    660
aaaatgcaaa aaaattagc cgggcgtggt ggcaggcacc tgtagtccca gctactcggg     720
aggctgaggc aggagactgg cgtgaaccca ggaggcggac cttgtagtga gccgagatcg    780
cgccactgtg ctccagcctg gcaacagag caagactcca tctcaaaaaa taaaaataaa     840
taaaaaataa aaaataaaa gagcaaacta tttccaaata ccatagaata acttacataa     900
aagtaatata actgtattgt aagtagaagc tagcactgg                           939
```

```
<210> SEQ ID NO 9
<211> LENGTH: 20
<212> TYPE: DNA
<213> ORGANISM: Homo sapiens

<400> SEQUENCE: 9 ggcgggggc gcacagagcc                                                 20

<210> SEQ ID NO 10
<211> LENGTH: 22
<212> TYPE: DNA
<213> ORGANISM: Homo sapiens

<400> SEQUENCE: 10
gagatggagt cttgctctgt tg                                             22

<210> SEQ ID NO 11
<211> LENGTH: 21
<212> TYPE: DNA
<213> ORGANISM: Homo sapiens

<400> SEQUENCE: 11
acagagtgga ataagacaga g                                              21

<210> SEQ ID NO 12
<211> LENGTH: 21
<212> TYPE: DNA
<213> ORGANISM: Homo sapiens

<400> SEQUENCE: 12
ccagtgctag cttctactta c                                              21

<210> SEQ ID NO 13
<211> LENGTH: 425
<212> TYPE: PRT
<213> ORGANISM: Homo sapiens

<400> SEQUENCE: 13
```

-continued

```
Met Gly Pro Arg Arg Leu Leu Val Ala Ala Cys Phe Ser Leu Cys
 1               5                  10                  15

Gly Pro Leu Leu Ser Ala Arg Thr Arg Ala Arg Pro Glu Ser Lys
             20                  25                  30

Ala Thr Asn Ala Thr Leu Asp Pro Arg Ser Phe Leu Leu Arg Asn Pro
         35                  40                  45

Asn Asp Lys Tyr Glu Pro Phe Trp Glu Asp Glu Lys Asn Glu Ser
 50                  55                  60

Gly Leu Thr Glu Tyr Arg Leu Val Ser Ile Asn Lys Ser Ser Pro Leu
 65                  70                  75                  80

Gln Lys Gln Leu Pro Ala Phe Ile Ser Glu Asp Ala Ser Gly Tyr Leu
             85                  90                  95

Thr Ser Ser Trp Leu Thr Leu Phe Val Pro Ser Val Tyr Thr Gly Val
            100                 105                 110

Phe Val Val Ser Leu Pro Leu Asn Ile Met Ala Ile Val Phe Ile
         115                 120                 125

Leu Lys Met Lys Val Lys Lys Pro Ala Val Val Tyr Met Leu His Leu
130                 135                 140

Ala Thr Ala Asp Val Leu Phe Val Ser Val Leu Pro Phe Lys Ile Ser
145                 150                 155                 160

Tyr Tyr Phe Ser Gly Ser Asp Trp Gln Phe Gly Ser Glu Leu Cys Arg
                165                 170                 175

Phe Val Thr Ala Ala Phe Tyr Cys Asn Met Tyr Ala Ser Ile Leu Leu
            180                 185                 190

Met Thr Val Ile Ser Ile Asp Arg Phe Leu Ala Val Val Tyr Pro Met
        195                 200                 205

Gln Ser Leu Ser Trp Arg Thr Leu Gly Arg Ala Ser Phe Thr Cys Leu
        210                 215                 220

Ala Ile Trp Ala Leu Ala Ile Ala Gly Val Val Pro Leu Val Leu Lys
225                 230                 235                 240

Glu Gln Thr Ile Gln Val Pro Gly Leu Asn Ile Thr Thr Cys His Asp
                245                 250                 255

Val Leu Asn Glu Thr Leu Leu Glu Gly Tyr Tyr Ala Tyr Tyr Phe Ser
            260                 265                 270

Ala Phe Ser Ala Val Phe Phe Phe Val Pro Leu Ile Ile Ser Thr Val
        275                 280                 285

Cys Tyr Val Ser Ile Ile Arg Cys Leu Ser Ser Ala Val Ala Asn
290                 295                 300

Arg Ser Lys Lys Ser Arg Ala Leu Phe Leu Ser Ala Ala Val Phe Cys
305                 310                 315                 320

Ile Phe Ile Ile Cys Phe Gly Pro Thr Asn Val Leu Leu Ile Ala His
                325                 330                 335

Tyr Ser Phe Leu Ser His Thr Ser Thr Thr Glu Ala Ala Tyr Phe Ala
            340                 345                 350

Tyr Leu Leu Cys Val Cys Val Ser Ser Ile Ser Ser Cys Ile Asp Pro
        355                 360                 365

Leu Ile Tyr Tyr Tyr Ala Ser Ser Glu Cys Gln Arg Tyr Val Tyr Ser
370                 375                 380

Ile Leu Cys Cys Lys Glu Ser Ser Asp Pro Ser Ser Tyr Asn Ser Ser
385                 390                 395                 400
```

```
Gly Gln Leu Met Ala Ser Lys Met Asp Thr Cys Ser Ser Asn Leu Asn
            405                 410                 415

Asn Ser Ile Tyr Lys Lys Leu Leu Thr
            420             425
```